US010736492B2

(12) United States Patent
Gat et al.

(10) Patent No.: US 10,736,492 B2
(45) Date of Patent: Aug. 11, 2020

(54) METHOD AND SYSTEM FOR MOVING AN IN-VIVO DEVICE IN THE GASTROINTESTINAL TRACT

(71) Applicant: GIVEN IMAGING LTD., Yoqneam Ilite (IL)

(72) Inventors: Daniel Gat, Zichron Yaakov (IL); Tomer Carmeli, Alonei Abba (IL)

(73) Assignee: GIVEN IMAGING LTD., Yoqneam Ilite (IL)

( * ) Notice: Subject to any disclaimer, the term of this patent is extended or adjusted under 35 U.S.C. 154(b) by 327 days.

(21) Appl. No.: 14/898,747

(22) PCT Filed: Jun. 12, 2014

(86) PCT No.: PCT/IL2014/050534
§ 371 (c)(1),
(2) Date: Dec. 16, 2015

(87) PCT Pub. No.: WO2014/207738
PCT Pub. Date: Dec. 31, 2014

(65) Prior Publication Data
US 2016/0135668 A1 May 19, 2016

Related U.S. Application Data

(60) Provisional application No. 61/840,184, filed on Jun. 27, 2013.

(51) Int. Cl.
*A61B 1/00* (2006.01)
*A61B 1/04* (2006.01)
*A61B 5/06* (2006.01)

(52) U.S. Cl.
CPC .......... *A61B 1/00158* (2013.01); *A61B 1/041* (2013.01); *A61B 5/062* (2013.01)

(58) Field of Classification Search
CPC ........................... A61B 1/041; A61B 1/00158
See application file for complete search history.

(56) References Cited

U.S. PATENT DOCUMENTS

| | | |
|---|---|---|
| 2004/0050394 A1 | 3/2004 | Jin |
| 2004/0138552 A1* | 7/2004 | Harel ............... A61B 1/00158 600/407 |
| 2005/0143647 A1 | 6/2005 | Miniai |
| 2005/0187479 A1 | 8/2005 | Graumann et al. |
| 2007/0038063 A1 | 2/2007 | Kuth et al. |
| 2007/0100200 A1* | 5/2007 | Suzuki ............... A61B 1/00151 600/101 |
| 2008/0139883 A1 | 6/2008 | Uchiyama |

(Continued)

OTHER PUBLICATIONS

International Search Report of Application No. PCT/IL2014/050534 dated Oct. 10, 2014.

*Primary Examiner* — Alexandra L Newton
(74) *Attorney, Agent, or Firm* — Pearl Cohen Zedek Latzer Baratz LLP

(57) ABSTRACT

An in-vivo device may be propelled in the gastrointestinal tract by a magnetic force such that the direction of the magnetic force applied to the in-vivo device follows, or is continually adapted to, the instantaneous spatial orientation of the in-vivo device. As the in-vivo device changes orientation in the gastrointestinal tract by the wall of the gastrointestinal tract, so does the magnetic force, to follow suit.

3 Claims, 9 Drawing Sheets

(56) References Cited

U.S. PATENT DOCUMENTS

| | | | | |
|---|---|---|---|---|
| 2010/0022835 A1* | 1/2010 | Kimura | ............ | A61B 1/00158 600/118 |
| 2010/0179782 A1* | 7/2010 | Kimura | ............ | A61B 1/00158 702/94 |
| 2010/0268026 A1* | 10/2010 | Takizawa | ........... | A61B 1/00158 600/109 |
| 2011/0181273 A1* | 7/2011 | Iida | .................... | A61B 1/00158 324/207.11 |
| 2011/0301497 A1 | 12/2011 | Sachar et al. | | |
| 2012/0149981 A1* | 6/2012 | Khait | ................ | A61B 1/00158 600/109 |
| 2013/0080119 A1 | 3/2013 | Khait et al. | | |

* cited by examiner

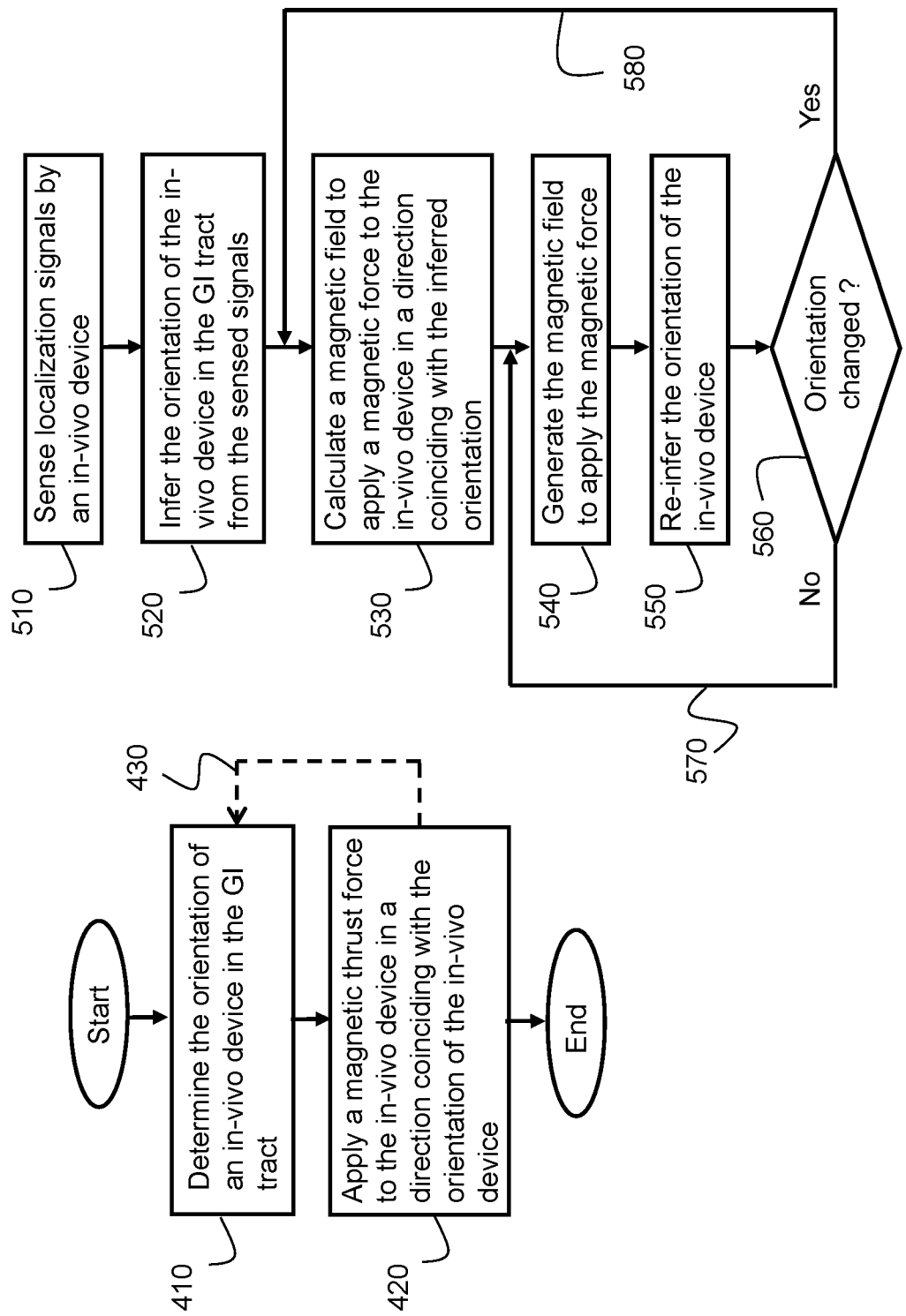

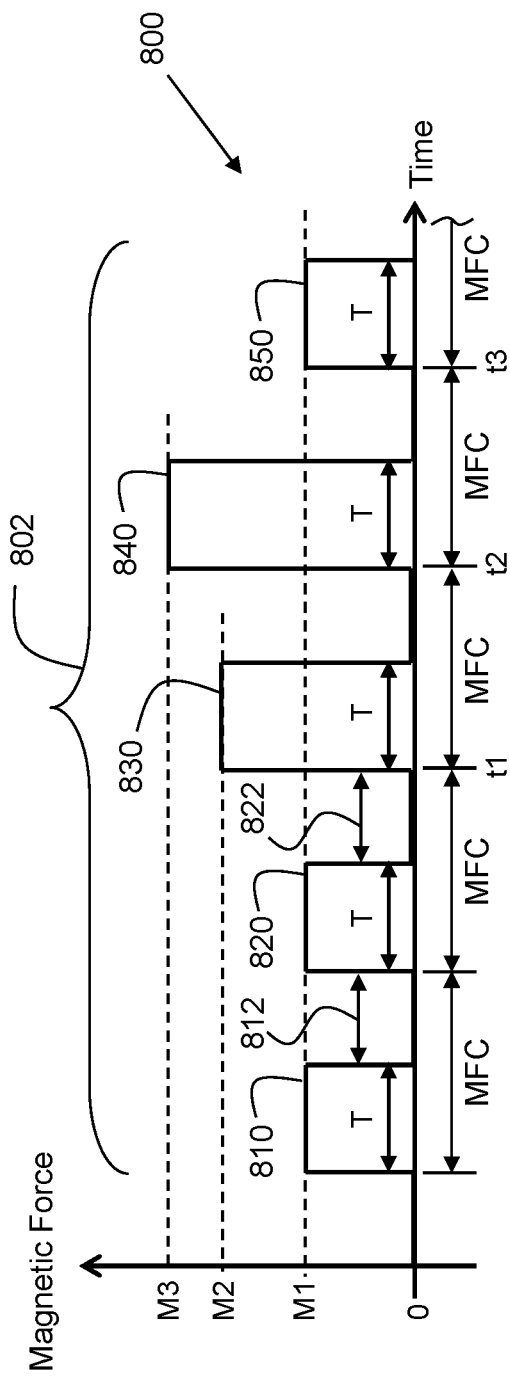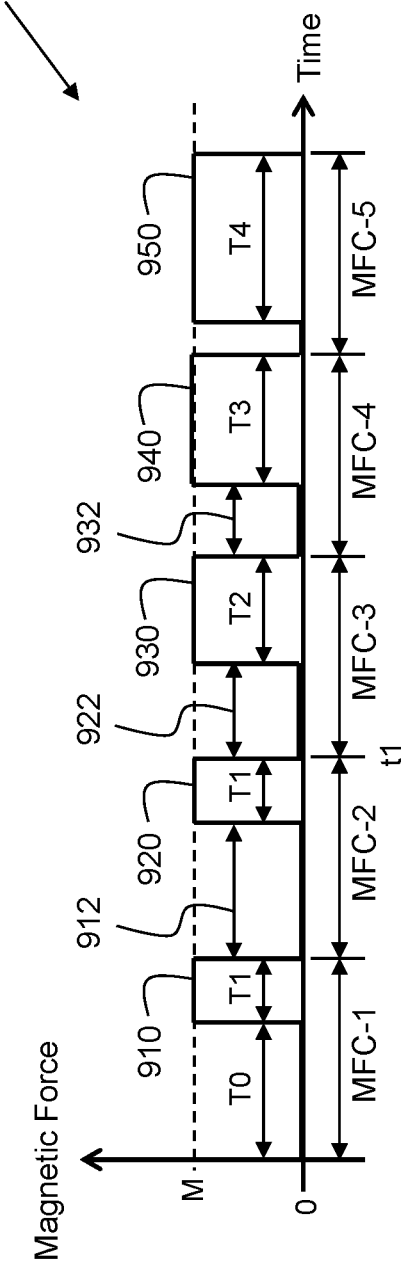

METHOD AND SYSTEM FOR MOVING AN IN-VIVO DEVICE IN THE GASTROINTESTINAL TRACT

CROSS-REFERENCE TO RELATED APPLICATIONS

This application is a National Phase Application of PCT International Application No. PCT/IL2014/050534, International Filing Date Jun. 12, 2014, entitled "Method and System for Moving An In-Vivo Device in the Gastrointestinal Tract", published on Dec. 31, 2014 as International Patent Application Publication No. WO 2014/207738, claiming priority of U.S. Provisional Patent Application No. 61/840,184, filed Jun. 27, 2013, which is incorporated herein by reference in its entirety.

FIELD OF THE INVENTION

The present invention generally relates to an in-vivo system and more specifically to a method for moving an in-vivo device in, and navigating it by, the gastrointestinal ("GI") tract, and to an in-vivo system and localization signal system implementing the method.

BACKGROUND

In-vivo measuring systems are known in the art. Some in-vivo devices/systems that traverse the gastrointestinal (GI) system may include one or more imaging sensors, for imaging (e.g., capturing images of) the interior of the GI system, and/or sensors of other types. In-vivo devices may traverse the GI system by being pushed through the GI system by peristaltic force exerted thereon by the digestive system, or by being maneuvered, for example, magnetically. Some maneuvering applications require 'knowing' a current location of the in-vivo device and a target/next location of the in-vivo device in order to generate a magnetic field that moves the in-vivo device from its current location to the target/next location or destination. However, detecting the location of an in-vivo device in the GI system requires a robust localization system and computing resources, and defining the target/next location of the device is not trivial (e.g., a three-dimensional model of the GI system may have to be defined). In addition, if the orientation of the in-vivo device is manipulatable, for example magnetically, trying to move the in-vivo device in one direction while the in-vivo device is oriented in another direction, this might be hazardous to the wall/tissue of the GI system.

It would be beneficial to have a method and system that simplifies magnetic maneuvering of an in-vivo device, for example, in the GI tract, and reduces potential hazards involved in such maneuvering.

SUMMARY

A method and system may magnetically thrust/propel a swallowable in-vivo device in the GI tract while adapting the spatial direction of the magnetic force that propels the in-vivo device to the spatial orientation of the in-vivo device in the GI system.

The in-vivo device may have a longitudinal axis passing through two, opposite, ends of the in-vivo device, and include a permanent magnet (or an electromagnet). The longitudinal axis may be used to define, or be indicative of, a spatial orientation of the in-vivo device. Embodiments of the invention may include positioning the magnet, or electromagnet, in one end of the in-vivo device, which is referred to herein as a 'magnetic thrusting end' ("MTE"), possibly on the in-vivo device's longitudinal axis, or the permanent magnet, or electromagnet, may have an axis which may be adjacent to the in-vivo device's longitudinal axis. The permanent magnet, or electromagnet, in conjunction with an external magnetic field, may facilitate generation of a magnetic thrusting or propelling force to move the in-vivo device magnetically in the GI tract (e.g., in the small bowel) while the other end of the in-vivo device, which is referred to herein as a "steerable end/head" and "guided end/head" and is opposite to the in-vivo device's MTE, e.g., with respect to, or along, the longitudinal axis of the in-vivo device, is freely (free to be) steered (e.g., free to change orientation/direction) by the wall of the GI tract as the in-vivo device advances (e.g., by peristalsis), or is advanced (e.g., thrust or propelled), through the GI tract. The in-vivo device may also include an orientation sensor to facilitate detection of the instantaneous spatial orientation of the in-vivo device.

In some embodiments, a method for maneuvering an in-vivo device in the GI tract may include determining a spatial orientation of the in-vivo device in the GI tract, and applying a magnetic force to the in-vivo device (to thrust, propel or push it) in a direction coinciding with or matching the spatial orientation of the in-vivo device. The spatial orientation of the in-vivo device may be defined according to, or based on, or be a direction of the longitudinal axis of the in-vivo device. In some embodiments, determining the spatial orientation of the in-vivo device may include generating localization electromagnetic field(s), sensing the electromagnetic field(s) by an orientation sensor contained in the in-vivo device, and determining or calculating the spatial orientation of the in-vivo device from signal(s) that the orientation sensor outputs in response to the sensed electromagnetic field(s). In some embodiments, sensing the electromagnetic fields may be by electromagnetic field sensing coils. In some embodiments, the magnetic force applied to the in-vivo device may be a magnetic thrust force. In some embodiments, generating the magnetic thrust force to move the in-vivo device may include generating a magnetic field that, jointly with a magnetic thrust unit ("MTU") that is included in the in-vivo device, generates the magnetic thrust force in a direction coinciding with the (sensed) spatial orientation of the in-vivo device.

In some embodiments, determining the spatial orientation of the in-vivo device and generating the magnetic thrust force that moves, thrusts or propels the in-vivo device may be performed at different times. For example, generation of the magnetic thrust force may be performed a short while (e.g., a few milliseconds) after the orientation of the in-vivo device is determined. In other embodiments, generating the magnetic thrust force may be concurrent to the determination of the orientation of the in-vivo device. (By 'concurrent' is meant overlapping in time, or as soon as time constraints, latency, etc., of the involved system enable to generate a magnetic thrust force following determination of the device's orientation.)

In some embodiments, the spatial orientation of the in-vivo device may be determined n times per second ('n'—an integer), for example approximately once per second (n=1). In some embodiments, the magnetic thrust force may be generated and applied constantly or continually between successive determinations of the orientation of the in-vivo device, assuming that the orientation of the in-vivo device does not change, or a change is within a permissible margin, between two successive determinations. In other embodiments, the magnetic thrust force may be applied intermittently between successive determinations of the orientation of the in-vivo device. In some embodiments, the orientation of the in-vivo device may be determined n times between successive magnetic force activations (MFAs), for example three times (n=3) between each two successive MFAs. In some embodiments, the MTF may be applied or activated n times between successive determinations of the orientation of the in-vivo device, for example two times (n=2) between each two successive orientation determinations.

In some embodiments, a method for maneuvering an in-vivo device in the gastrointestinal tract may include generating localization electromagnetic fields, sensing the electromagnetic fields by an orientation sensor included in an in-vivo device moving in the GI tract, determining or calculating a spatial orientation of the in-vivo device from the sensed electromagnetic fields, and generating a magnetic field to induce a magnetic thrust force in a magnetic thrust unit (MTU) included in the in-vivo device, in a direction coinciding with the spatial orientation of the in-vivo device.

In some embodiments, a system for maneuvering an in-vivo device in the GI tract may include a localization signal system/source ("LSS") to generate localization electromagnetic fields; a magnetic maneuvering system to generate maneuvering magnetic field(s); and an in-vivo device having a longitudinal axis that may define a spatial orientation of the in-vivo device. (The spatial orientation of the in-vivo device may be defined in a different way; e.g., by an orientation of any component contained in the in-vivo device; e.g., by an orientation of the orientation sensor or magnetic thrust unit.) The in-vivo device may include an orientation sensor to facilitate determination of the spatial orientation of the in-vivo device by sensing localization electromagnetic fields generated by the localization signal system. The in-vivo device may also include a magnetic thrust unit (MTU) to apply, in conjunction or jointly with the maneuvering magnetic field generated by the magnetic maneuvering system, a magnetic thrust force to the in-vivo device, wherein the magnetic maneuvering system may be configured to generate the magnetic field such that the magnetic force may be applied to the MTU, hence to the in-vivo device, in a direction coinciding with the (sensed) orientation of the in-vivo device. The MTU may be positioned in one end of the in-vivo device (e.g., in the MTE), possibly off the center of mass of the in-vivo device, or at or approximately at the center of mass. The MTU may be configured and positioned in the in-vivo device in a position facilitating application of the magnetic thrust force in the direction coinciding with the spatial orientation of the in-vivo device. In some embodiments, the orientation sensor included in the in-vivo device may include one electromagnetic field sensing coil. In other embodiments, the orientation sensor may include two electromagnetic field sensing coils, or more than two electromagnetic field sensing coils. In some embodiments, the magnitude and/or the activation period of the magnetic thrust force may depend on one parameter or on more than one parameter (e.g., two parameters), which may be selected from the group consisting of: the orientation of the in-vivo device, the location of the in-vivo device and the velocity of the in-vivo device.

In some embodiments, a method is provided for navigating an in-vivo device by the GI tract, where the in-vivo device may comprise a magnetic thrust end and a steerable head opposite to and spaced apart from the magnetic thrust end, and the magnetic thrust end may comprise a magnetic thrust unit, the method may include (i) determining a three-dimensional orientation of the in-vivo device in the gastrointestinal tract; and (ii) moving the in-vivo device in the GI tract by applying a magnetic force cycle ("MFC"), the MFC may include a time period, which is referred to herein as a 'magnetic force activation' ("MFA") period, during which a magnetic thrust force (MTF) may be induced in the magnetic thrust unit (MTU) so as to move the in-vivo device in a direction coinciding with the determined orientation of the in-vivo device. The MFC may also include another period, which is referred to herein as an 'orientation settling period', during which no MTF is induced, or only a relatively low MTF is induced, in the MTU, in order to enable the in-vivo device's orientation to settle naturally in-between successive MFAs. ('Settle naturally' means the in-vivo device is allowed to be freely oriented by the GI tract.) Steps (i) and (ii) may be repeated or reiterated; e.g., to move the in-vivo device further, or farther, in the GI tract. The method may further include comparing an actual velocity of the in-vivo device in the gastrointestinal tract to a reference velocity that may be, for example, an expected velocity or a desired velocity, and changing a parameter of the MTF according to a (calculated) difference between the actual velocity and the reference velocity. The method may further include changing the parameter to reduce the difference between the actual (calculated) velocity and the reference velocity. The MTF's parameter may be selected from the group consisting of a magnitude of the magnetic force and a duty cycle of the magnetic force cycle. The reference velocity may depend (e.g., selected based) on a location of the in-vivo device in the GI tract, or on the orientation of the in-vivo device, or on both location and orientation of the in-vivo device.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIG. 4 depicts a method for navigating an in-vivo device according to an embodiment of the invention;

FIG. 5 depicts a method for navigating an in-vivo device according to another embodiment of the invention;

FIG. 8 shows an example timing diagram according to some embodiments of the invention;

FIG. 9 shows an example timing diagram according to other embodiments of the invention;

DETAILED DESCRIPTION

Figure 1:
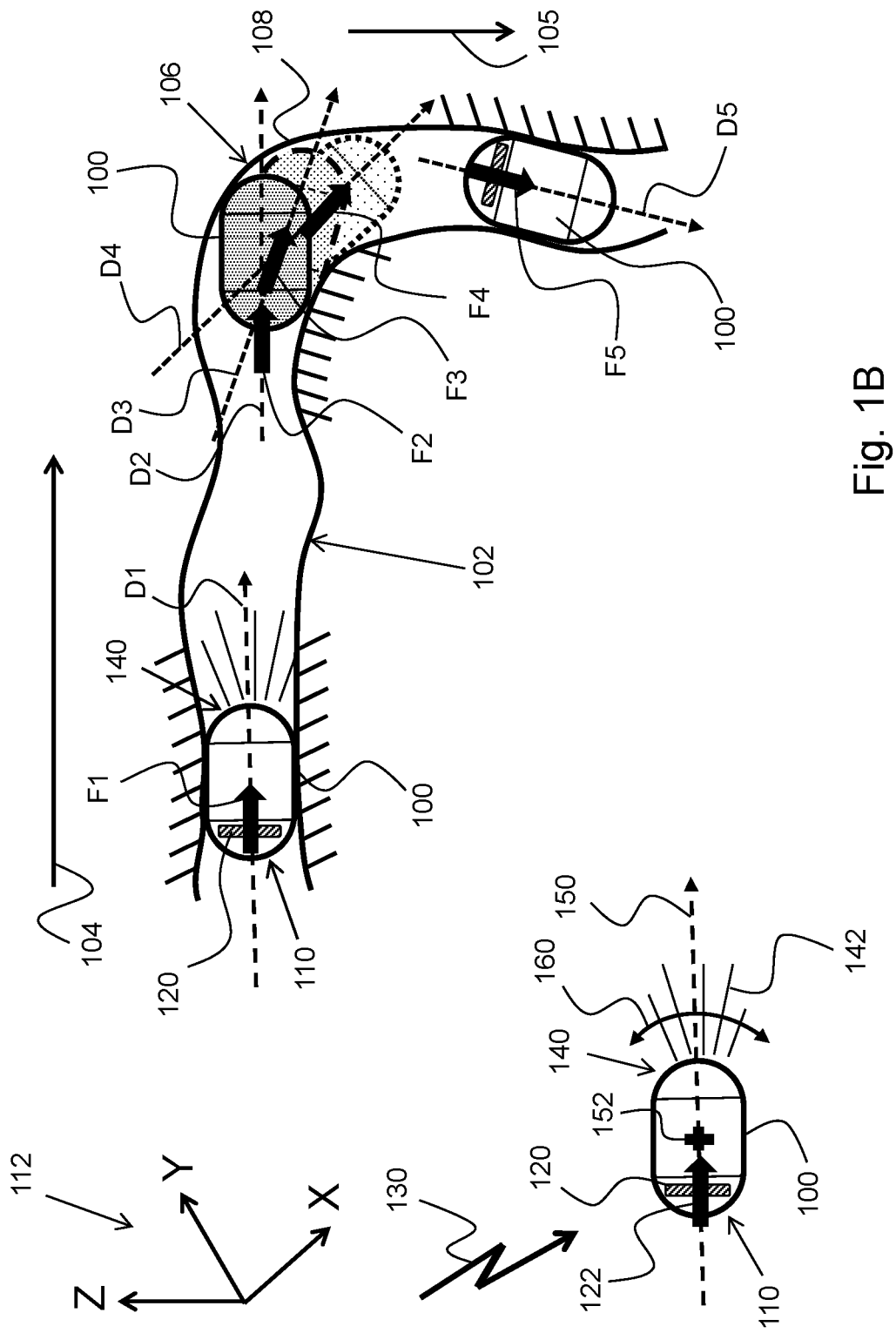
FIGS. 1A and 1B schematically illustrate a method for moving an in-vivo device in a GI tract according to an example embodiment of the invention.

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not constrained to a particular order or sequence. Additionally, some of the described method embodiments or elements thereof can occur or be performed at the same time.

An untethered in-vivo device (e.g., a capsule-shaped endoscope) may be effectively moved (e.g., magnetically) in narrow portions of the GI tract (e.g., especially in the small intestine, possibly in the large intestine), by knowing the spatial (3-D) orientation, and optionally the location, of the in-vivo device, because narrow GI portions impose their orientation on the in-vivo device as the in-vivo device moves through them, so, knowing the device's instantaneous orientation and pushing it (e.g., magnetically) in that direction ensures easy maneuvering and navigation of the device, with reduced navigation-related hazards that may be associated with; e.g., lateral movement of the in-vivo device. ('Narrow portion' means a GI portion having a size small enough to peripherally, or substantially peripherally, wrap the in-vivo device.) The system and methods disclosed herein may be effective both in cases where an in-vivo device includes an image sensor and in cases where an in-vivo device does not include an image sensor. In addition, using the system and methods disclosed herein enable moving an in-vivo device through long GI distances (e.g., in small bowel) with no need for human intervention because the maneuvering process disclosed herein can be fully automatic.

The orientation, or the location, or both the orientation and location of the in-vivo device may be used to determine the magnitude of the magnetic thrust force (MTF) and/or the period during which the MTF is applied/activated. For example, if, per the sensed orientation, the in-vivo device is ascending, the magnetic thrust force may be increased to compensate for the adversary gravity force, and vice versa. Using, for example, pH measurements taken by a pH sensor included in the in-vivo device may be used to detect when the device leaves the stomach and enters the small bowel, and the magnitude and/or the activation period of the MTF applied to the MTU may be adjusted or changed accordingly, manually or automatically.

The magnitude of the MTF and/or the period during which the MIT is applied/activated may be set according to a target location or orientation (e.g., depending on a difference between a current location/orientation of the in-vivo device and a target location/orientation thereof), and/or according to the velocity of the in-vivo device.

The velocity of the in-vivo device may also be used to determine the magnitude and/or the duration/period of the magnetic thrust force. (The velocity of the in-vivo device may be assessed for example using location information.) In some embodiments, if the in-vivo device is moving relatively slow (e.g., it moved a few millimeters when it should had moved, or expected to move, a few centimeters), the magnitude of the magnetic thrust force may be increased temporarily or momentarily, for example during the next 2-4 activations of the magnetic force, and vice versa, where 'activation' means a short application, or inducing a 'burst', of the magnetic thrust force, for example for half a second per activation, or so. In some embodiments, activations of the magnetic force may reoccur in cycles ('magnetic force cycles', or "MFC") and, optionally, according to a duty cycle that may change according to the velocity of the in-vivo device. In other embodiments, if the in-vivo device is moving relatively slow, the duty cycle of n (n=1, 2, 3, ... ) subsequent magnetic force cycles may temporarily or momentarily be increased in order to lengthen the period of the magnetic thrust force, whose magnitude may be constant during that time or manipulated as well.

In general, a magnetic thrust end (MTE) may include a magnetic thrusting unit (MTU) that may facilitate thrusting of, or propelling, the in-vivo device in the GI tract (e.g., in the small intestine) by using an external magnetic field. The in-vivo device may also have a steerable end/head (a guided end/head) located at a front end of the device, opposite to the device's MTE. The steerable head may be mechanically steered, or guided, by the wall of the GI; e.g., by a counterforce that the wall of the GI tract may, occasionally, exert on the in-vivo device when a side of device's head c the wall of the GI tract, which may cause the orientation of the in-vivo device to be changed. The in-vivo device may have a longitudinal axis that may pass through the device's MTU and steerable head.

As the in-vivo device moves in the GI tract (as a result of an interaction between an external magnetic field and the MTU, or as a result of peristalsis, or as a result of both forces), the spatial orientation of the in-vivo device may change as a result of the device's steerable head touching, and guided by, the GI tract's wall (e.g., when the GI's tract direction changes). The spatial orientation of the in-vivo device may be monitored constantly, continually or intermittently, and a maneuvering magnetic field may be generated such that the direction of the (thrusting) magnetic force, which is generated in conjunction with the magnetic thrust unit (MTU) residing in the in-vivo device, always follows (to coincide with) the spatial orientation of the in-vivo device. Application of a magnetic force to the in-vivo device in such a manner facilitates movement of the device in the GI tract by using minimal magnetic force (because, e.g., there is no need to generate magnetic fields to force the in-vivo device to change its orientation, as this is done naturally by the GI tract's wall). Application of a magnetic force to the in-vivo device in such a manner may also reduce potential maneuvering hazards because, for example, the chance that an in-vivo device might be forcefully driven into the GI tract's wall is low, in part because the tract's wall steers/diverts the device's steerable head away from the wall, back into the GI lumen. In addition, using the system and methods disclosed herein may relieve the medical staff of the need to steer through about a six-meter long small bowel; the system will do it automatically.

In general, an in-vivo device operating with an in-vivo device localization system may be capable, among other things, of: (i) transferring data frames to (and in some embodiments exchanging data with) an external receiver (e.g., external data recorder) with which the in-vivo device may operate, (ii) sensing localization signals (e.g., electromagnetic localization signals) that may be generated by an external system, (iii) processing the sensed localization signals and transmitting corresponding orientation data (and optionally also location data) to the data recorder. The localization data transmitted by, or from, the in-vivo device may represent the raw signal(s) that is/are induced in the in-vivo device by localization signals, and thus it may have to be processed by an external system in order to determine the orientation (and optionally the location) of the in-vivo device, for example, in the GI tract. Alternatively, the raw (localization) signals may be processed internally (by or in the in-vivo device), and the resultant localization data (orientation data, and optionally also location data) transmitted by or from the in-vivo device may represent the orientation (and optionally the location) of the in-vivo device. The external receiver (e.g., data recorder) may be configured, among other things, to: (i) wirelessly receive data (e.g., image frames) from the in-vivo device, and (ii) use orientation information/data to generate a magnetic field in order to magnetically push/thrust the in-vivo device in the direction of the instantaneous orientation of the in-vivo device.

In some embodiments, the system generating the localization signals may transmit localization signals at specific times and for specific durations which are preset for (and governed by) the in-vivo device because localization signals are to be transmitted to the in-vivo device only during time slots that the in-vivo device allocates or reserves for sensing this type of signals. This type of synchronization helps ensure that localization signals are transmitted to the in-vivo device only when the in-vivo device is ready to receive and process them. In general, a time slot (a period of time herein referred to as the "sensing window") may be allocated within each work cycle (e.g., within a transmission period of each work cycle, or within an idle period of each work cycle) or within selected work cycles according to which the in-vivo device operates. The sensing window may be used to sense localization signals that originate from an external localization signals source (LSS).

FIGS. 1A and 1B schematically illustrate a method for moving an in-vivo device 100 in a GI tract 102 according to an example embodiment of the invention. Referring to FIG. 1A, in-vivo device 100 may have two spaced apart, oppositely positioned, ends, or heads: a magnetic thrust end/head 110 that may include, contain, or have associated with it a magnetic thrust unit ("MTU") 120, and a steerable or guidable end 140. MTU 120 may include a permanent magnet, or an electromagnet, whose magnetic moment, M, points in a direction coinciding with, or parallel to, a longitudinal axis 150 of in-vivo device 100. MTU 120 may facilitate application of a magnetic thrust force (MTF) 122 (to thrust/propel in-vivo device 100 in the GI tract) whose direction coincides with a direction of longitudinal axis 150 of in-vivo device 100. The MIT may be induced by an (external) magnetic field 130 that may have a magnetic gradient in the direction of longitudinal axis 150, therefore in the direction of the magnetic moment, M, of the (electro) magnet included in MTU 120. (Since the magnetic moment, M, of the (electro)magnet and longitudinal axis 150 are parallel or coinciding, a magnetic gradient applied to the (electro)magnet in the direction of its magnetic moment, M, would result in a magnetic force, F, thrusting in-vivo device 100 in the direction of longitudinal axis 150.)

Steerable, or guidable, end/head 140 may be a front end/head of in-vivo device 100. Steerable, or guidable, end/head 140 may spatially be steered or guided (e.g., its orientation forced to change, as shown at 160, about a center of mass 152 of device 100) by a counterforce that the wall (102) of the GI tract may, occasionally, exert on it when steerable/guidable end/head 140 bumps into, or otherwise contact, the GI tract's wall (hence the term 'steerable end/head', or 'guidable end/head'). In-vivo device 100 may be configured such that center of mass (152) is interposed between magnetic thrust end/head 110 and steerable/guidable end/head 140, to facilitate easy steering/guiding of end/head 140 by the wall (102) of the GI tract while/when magnetic (thrust) force 122 is thrusting or propelling in-vivo device 100. (The magnetic thrust force applied to the in-vivo device is applied such that navigation of the device can be done by the GI tract steering the device's guidable end/head.)

In-vivo device 100 may include an imager for imaging, for example, the GI system, and a light source 142 for illuminating a site to be imaged by the imager. In-vivo device 100 may have longitudinal axis 150 that may pass through the device's magnetic thrust unit 120 and steerable head 140. Magnetic field 130 may be configured; e.g., its magnetic parameters may be devised such that interaction with magnetic thrust unit (MTU) 120 always results in a magnetic force whose direction coincides with, e.g. is in the same direction as (e.g., pointing in a direction of), longitudinal axis 150. (Magnetic force 122 and longitudinal axis 150 are shown in FIG. 1A having the same spatial direction, or pointing in the same direction or along the same vector; e.g., they may be coinciding.) If, for any reason, steerable head 140 changes (it is guided to another) direction (it moves, or forced to move, for example, upwards or downwards, as shown at 160), so does the magnetic force 122, in order to maintain the spatial alignment between the two orientations/directions—the orientation/direction of the magnetic force and the orientation/direction of the device. (Changing the orientation/direction of magnetic force 122 may be implemented in real time by controlling the magnetic parameters of magnetic field 130.) MTU 120 may be configured and positioned in in-vivo device 100, and magnetic field 130 may be configured, such that they jointly produce a magnetic thrust force (e.g., magnetic force 122) whose spatial direction matches that of the orientation of in-vivo device 100, as may be defined by; e.g., its longitudinal axis 150.

In general, the orientation of the in-vivo device and magnetic force may be, related to or indicate the way the in-vivo device and magnetic force are turned or are pointing in space, possibly relative to some reference frame. For example, the spatial direction of in-vivo device 100 (as defined or indicated by, for example, longitudinal axis 150), as well as the spatial direction of a vector representing magnetic force 122, may be determined, for example, relative to a reference coordinate system, for example relative to an X-Y-Z coordinate system shown at 112. (The three-dimensional (3-D) orientation of the in-vivo device and the 3-D orientation of the vector of the magnetic force may be defined in other ways, for example relative to other coordinate systems. Any orientation-defining method is eligible if it can be used to spatially align the vector of the magnetic force to the orientation of the in-vivo device.)

FIG. 1B schematically illustrates in-vivo device 100 in five, different, positions in GI tract 102. (Assume that in-vivo device 100 moves in GI tract 102 in direction 104.) At first, magnetic force F1 thrusts, pushes or propels in-vivo device 100 to the right (104) while the walls of GI tract 102 guide its steerable/guidable end/head 140 in direction D1. When in-vivo device 100 reaches (or bumps into) a turn 106 of GI tract 102, the curved wall of GI tract 102 starts to push steerable/guidable end/head 140 downwards (105) by applying a counter force that acts as a turning torque. As a result of the turning torque pushing steerable/guidable end/head 140 downwards, the orientation of in-vivo device 100, as a whole, may change to direction D2, with the direction of the magnetic thrust force F2 following suit (adapting to or following the new orientation, D2, of the in-vivo device). With the counterforce still exerted on steerable/guidable end/head 140 by wall region 108 of GI tract 102 while magnetic thrust force F2 acts, the spatial orientation of in-vivo device 100 continues to smoothly or gradually change from orientation/direction D2 to orientation/direction D3, and, then, from orientation/direction D3 to orientation/direction D4, with the orientation/direction of the magnetic thrust force following suit; namely, with the magnetic thrust force changing from magnetic thrust force F2 to magnetic thrust force F3 to adhere to, or to comply with, or to follow orientation/direction D3, and, then, changing from magnetic thrust force F3 to magnetic thrust force F4 to adhere to, or to comply with, or to follow orientation/direction D4 of in-vivo device 100. That is, when the orientation of in-vivo device 100 changes, for example due to a turning torque exerted, for example, by the turning wall 106 of GI tract 102, the spatial (3-D) orientation/direction of the magnetic thrusting force that thrusts or propels in-vivo device 100 may also change to follow, or match, the spatial (3-D) orientation/direction of in-vivo device 100.

When the in-vivo device moves in a relatively narrow portion/segment of the bended GI tract (e.g., a portion of the GI tract has twists/turns), the orientation of the in-vivo device (as determined/sensed) reliably represents, or embodies, the 'local' orientation of that GI portion/segment. Therefore, thrusting or propelling the in-vivo device in each particular GI portion in a direction that coincides with the in-vivo device's orientation, and therefore with a direction that matches that of the particular GI portion, ensures smooth transition of the in-vivo device in the GI tract in each GI portion and also from one GI portion to another.

When a magnetic field such as magnetic field 130 (FIG. 1A) is generated to produce the magnetic gradient that is required to induce, or produce, magnetic force F1, the magnetic field may also apply to the magnet (hence to in-vivo device 100) a torque, T, whose magnitude is a function of the magnetic field strength (B), the magnetic moment (M), and Sin(θ), where θ is the angle between B and M. If B and M are parallel/coincide (which means that T=0); i.e., they point to the same direction; e.g., to the direction of longitudinal axis 150 of in-vivo device 100, this means that the magnetic force thrusting/propelling in-vivo device 100 in the direction of its longitudinal axis (150) also stabilizes in-vivo device 100 in this direction. (In other words, the thrusting/propelling magnetic force also applies a stabilizing torque to the magnet, hence to the in-vivo device, which tends, or acts, to maintain the in-vivo device's direction.) Therefore, when in-vivo device 100 reaches turn 106, and assuming the thrusting/propelling force is applied continuously in the same direction (e.g., direction D1), the turning torque exerted by turning wall 106 of GI tract 102 may have to be greater than the stabilizing torque exerted by the thrusting/propelling magnetic field in order to effect the turn (to change the orientation to follow the GI bend). This problem may be solved or mitigated by, for example, applying the thrusting/propelling magnetic force in pulses, in a 'thrust-and-settle' ("T&S") mode. The thrust-and-settle mode may include or involve generation of the thrusting/propelling magnetic field in bursts, where each thrusting/propelling magnetic field burst momentarily accelerates the in-vivo device, and letting the in-vivo device's orientation to settle (e.g., letting it change only by the wall of the GI tract) in-between each two consecutive thrusting/propelling magnetic field bursts. This problem may also be solved by, for example, manipulating the intensity of the thrusting magnetic field. For example, the intensity, or strength, of the thrusting magnetic field may be selected such that the stabilizing effect of (the adversary stabilizing torque caused by) the thrusting magnetic field is reduced to a non-interfering value/level.

Some studies (in/ex-vivo animal tests) suggest that the force required to move an in-vivo device in the small intestine has been roughly estimated to be approximately in the range of 20-40 gram-force. Other studies suggest that, moving an in-vivo device in the small intestine requires a minimal force range of 15-20 gram-force. In general, the force required to move a content, be it bolus or an in-vivo device, depends on various factors, many of which are statistical, such as the dimensions, shape and surface properties of the content/device, the bowel's diameter, in-vivo device's speed, gut segment orientation relative to gravity direction/force, tonus of the bowel's muscles, etc. For example, if an in-vivo device moves in a relatively 'lenient' environment where the bowel's diameter is large, the bowel's muscles are feeble/weak (their tonus is low) and the in-vivo device descends in the direction of gravity, a small magnetic force (e.g., 5 gram-force) might suffice to move the in-vivo device.

Figure 2:
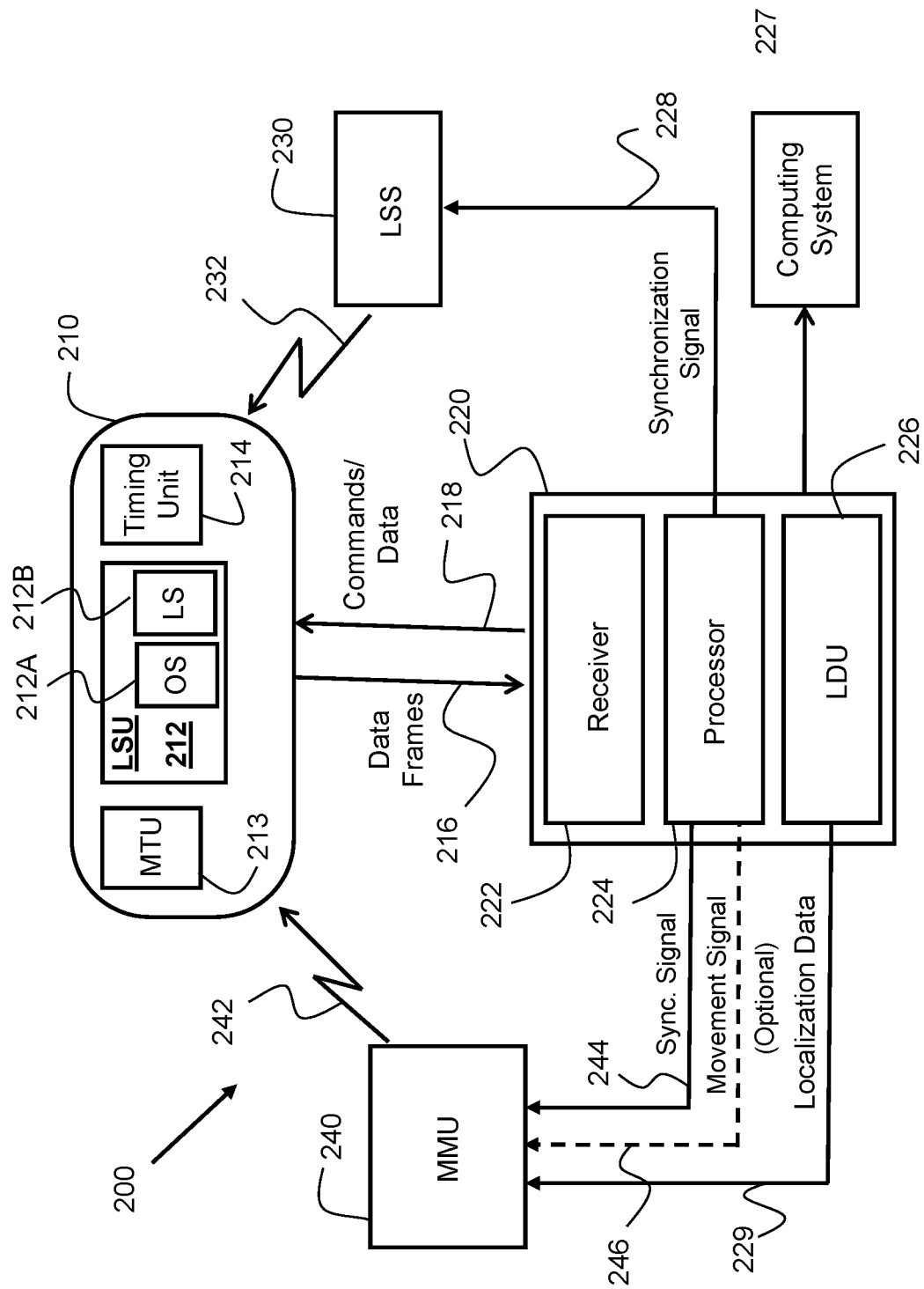
FIG. 2 is a block diagram of an in-vivo device maneuvering system according to an example embodiment.

FIG. 2 is block diagram of an in-vivo device maneuvering system 200 according to an example embodiment. In-vivo system 200 may include an in-vivo device 210, a data recorder 220, a localization signal system/source ("LSS") 230, and a magnetic field generating system 240 referred to herein as a magnetic maneuvering unit ("MMU"). In-vivo device 210 may be configured to sense a physical parameter in vivo. Temperature, pH, pressure and impedance are example physical parameters. In-vivo device 210 may sense other physical parameters and/or be capable of performing various surgical operations in vivo. In-vivo device 210 may capture images (e.g., take pictures) in vivo (e.g., of the GI system). In-vivo device 210 may include a transmitter for transmitting data, for example to data recorder 220, which is related to sensed physical parameter and/or related to or representing captured images. In-vivo device 210 may transmit the data in the form of 'frames', where each frame may include any type of data, for example image data related to a captured image. LSS 230 may generate electromagnetic fields, which are referred to herein as 'localization signals', to facilitate determination of the orientation and, optionally, location of in-vivo device 210. MMU 240 may generate magnetic fields, which are referred to herein as 'maneuvering signals', to facilitate maneuvering of in-vivo device 210. In-vivo device 210, LSS 230 and MMU 240 may orchestrate in synchronization with each other such that no system is interfered with by any other system, and LSS 230 generates the localization signal at times when in-vivo device 210 is ready to sense and process them.

In-vivo device 210 may also include a localization sensing unit ("LSU") 212 for sensing localization signals generated by an external localization system, for example by localization signals source (LSS) 230. LSU 212 may include an orientation sensor (212A) to facilitate determination or calculation of the spatial orientation of in-vivo device 210, and, optionally, a location sensor (212B) to facilitate determination or calculation of the spatial orientation of in-vivo device 210. LSU 212 may include one electromagnetic sensing coil, or another electromagnetic field detector, or more than one (e.g., two or three) electromagnetic sensing coils, or other electromagnetic field detectors for sensing an electromagnetic field. The electromagnetic field detectors may be mutually perpendicular. Each electromagnetic sensing coil, or electromagnetic detector, of LSU 212 may sense an electromagnetic field in a different direction and/or different orientation. For example, one coil of LSU 212 may sense a component of an electromagnetic field in the 'X' direction or orientation, another coil may be used to sense a component of an electromagnetic field in the 'Y' direction, or orientation, etc. Each localization signal generated by LSS 230 may induce an electromotive force ("EMF") signal induced in, or sensed by, the electromagnetic sensing coil(s) of LSU 212, and the instantaneous orientation, and optionally the instantaneous location, of in-vivo device 210 may be determined, calculated or inferred from, or based on, the EMF signal sensed by the sensing coil(s) of LSU 212. In-vivo device 210 may also include a timing unit 214 for scheduling time specifics (e.g., starting time and duration) of a sensing window during which LSU 212 may be activated and the EMF signals induced in, or sensed by, LSU 212, and measured. LSU 212 may function as (e.g., include only) a location sensor, or as (e.g., include only) an orientation sensor, or as an orientation and location sensor (e.g., include both sensors). For example, LSU 212 may function, at times, as a location sensor, and at other times as an orientation sensor. In-vivo device 210 may also include a magnetic thrust unit ("MTU") 213 to facilitate magnetic thrusting of in-vivo device 210. MTU 213 may be positioned in one end of in-vivo device 210 (this end is referred to herein as "thrusting end"), off the center of mass of in-vivo device 210.

Data recorder 220 may include, among other things, a receiver 222, a data storage unit (not shown in FIG. 2), a processor 224, and a localization data unit ("LDU") 226. Receiver 222 may receive (216) data frames from in-vivo device 210. Data recorder 220 may also include a transmitter (not shown in FIG. 2) for transmitting (218) commands and/or data to in-vivo device 210. For example, data recorder 220 may transmit a command to in-vivo device 210, for example, to change a mode of operation (e.g., an image capturing rate of an imager of the in-vivo device), or to update a parameter of the in-vivo device, etc.

LDU 226 may receive localization data originating from LSU 212, process the data to determine orientation, and optionally location, of in-vivo device 210, and, in some embodiments, output (229) localization data representative of the device's orientation (and, in some embodiments, also the device's location) to MMU 240. MMU 240 may generate a magnetic field (242) to move in-vivo device 210, and may set the magnetic characteristics of the magnetic field according to the in-vivo device's orientation data transferred to it (229) by LDU 226 as part of the localization data. That is, MMU 240 may generate a magnetic field (242) such that the magnetic field, in conjunction with the in-vivo device's magnetic thrust unit, induces a magnetic force in (substantially) the same direction as the spatial orientation of the in-vivo device. MMU 240 may be configured to generate the magnetic field continuously or intermittently while accounting for changes in the instantaneous orientation of in-vivo device 210.

Alternatively, processor 224 may process the localization signal, identify the instantaneous spatial orientation of in-vivo device 210, and output (246) a 'movement signal, or an instruction, to MMU 240, to generate a magnetic field corresponding to the instantaneous spatial orientation of in-vivo device 210.

Processor 224 may transfer (228) a synchronization signal to LSS 130, for example via a communication cable or wirelessly. Synchronization signal 228 may enable LSS 230 to correctly time the generation or production of one or more localization signals (in the form of electromagnetic field(s)). For example, LSS 230 may generate an electromagnetic field 232 at times and for durations set forth by, governed or complying with, synchronization signal 228. For example, LSS 230 may generate and transmit localization signal 232 exactly in time slot(s), or sensing windows, during which in-vivo device 210 uses LSU 212 to sense induced EMF signals and allocates resources that are required to process the induced EMF signals.

As a result of in-vivo device 210 sensing the induced EMF signals during a particular work cycle of the in-vivo device, or during a sensing window, in-vivo device 210 may embed data representative of the sensed EMF signals in a data frame that is transmitted (e.g., to a data recorder; e.g., to data recorder 220) during a transmission period, for example, of a work cycle, or sensing window, that follows the particular work cycle or sensing window. Data that represent the raw EMF signals, and any variant, manipulation, or derivative of such data (e.g., data representing the actual orientation, and optionally location, of the in-vivo device) is referred to herein as "localization data" and "sensing data". "Localization data" may, therefore, refer to data that is sensed by the in-vivo device; e.g., by LSU 212, and represents or indicates the orientation and, in some embodiments also the location, of the in-vivo device, or allows the in-vivo device to determine the orientation (and, if required, location) of the in-vivo device. Alternatively, localization data may be transmitted (e.g., to a data recorder) not by using the communication channel via which frames are transmitted, but by using a separate communication channel. Using a separate communication channel to transmit localization data may facilitate higher rates of transmission of localization data; i.e., transmission of larger amount of localization data per time unit.

Localization data unit (LDU) 226 may include or use a processor and other components and units that may be required to interpret, calculate, deduce, infer, or otherwise determine the orientation, and, optionally, also the location of in-vivo device 210 from the localization data. After LDU 226 determines the orientation/location of the in-vivo device, LDU 226 may transfer corresponding localization data 229 to another computing system. Localization data 229 may include data that represents the current orientation of in-vivo device 210, or the current location of in-vivo device 210, or both orientation and location of in-vivo device 210. The other computing system (e.g., computing system 227) may, for example, display the orientation/location data (whether the raw data or a processed version thereof), and/or it may use past and current orientation/location data to display, for example, the instantaneous spatial orientation of in-vivo device 210 and/or the instantaneous spatial orientation of the force acting on the in-vivo device. The route traversed, or distance travelled, by the in-vivo device may be displayed as well. The other computing system may also use localization data 229 to push in-vivo device 210 in the GI tract in a spatial direction corresponding, or following, the spatial orientation of the in-vivo device as measured, for example, by LSU 212.

Figure 3:
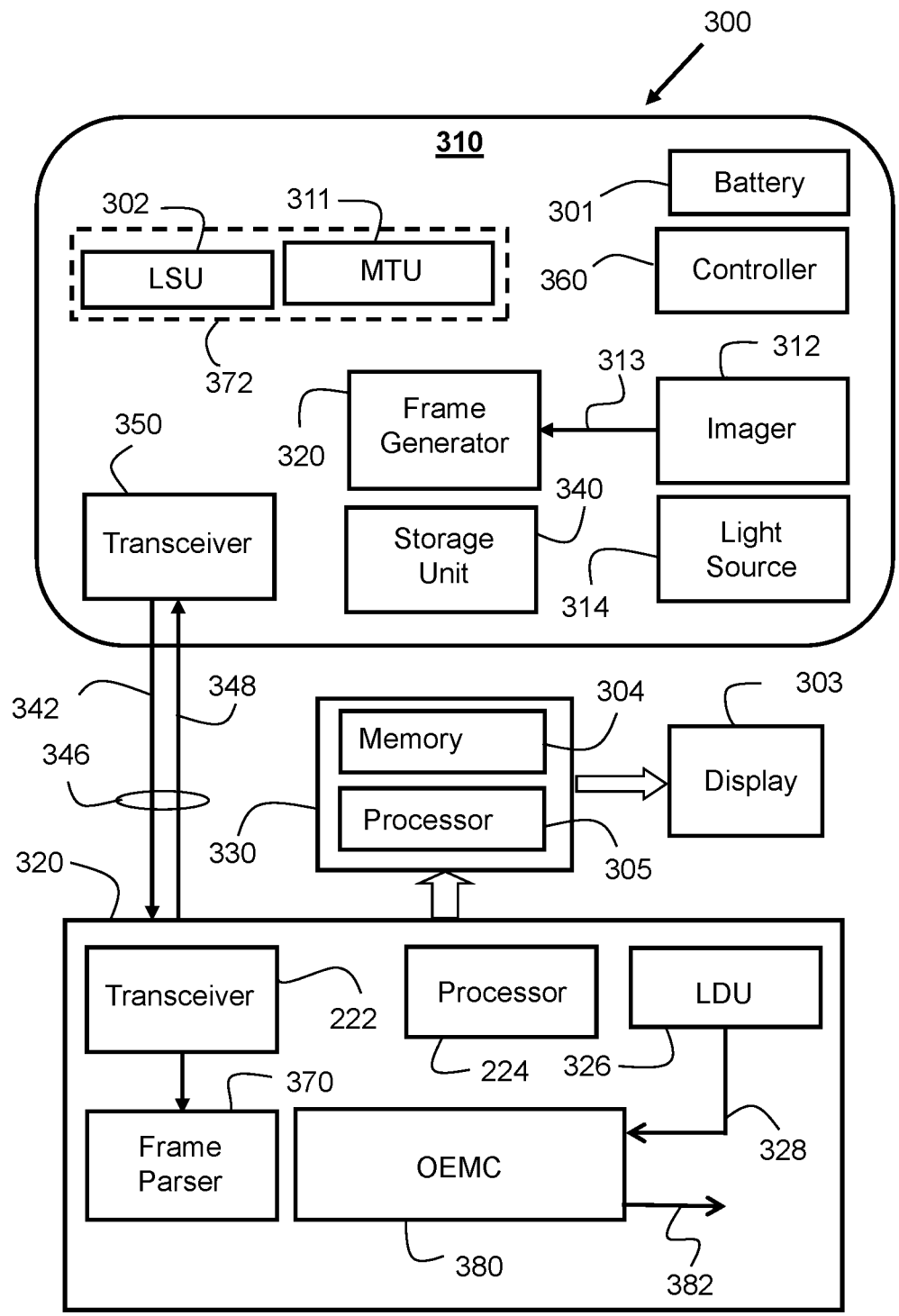
FIG. 3 shows an in-vivo imaging system according to an example embodiment.

LSU 212 may be part of a magnetic steering unit ("MSU"). (A MSU is shown in FIG. 3 at 372.) The MSU may include, for example, a permanent magnet. The permanent magnet of the MSU may interact with, for example, magnetic field 242 to produce a magnetic thrusting force to push the in-vivo device. MMU 240 may control the magnetic force propelling or pushing in-vivo device 110 based, for example, on orientation signals (e.g., representing localization data 229) that may be provided, or output, by LDU 226. The operation of MMU 240 may be synchronized to the operation of LSS 230 in order to ensure that there is no temporal overlap between maneuvering signal 242, which is generated by MMU 240, and localization signal 232, which is generated by LSS 130. This synchronization may be affected, for example, by data recorder 220 (e.g., by processor 224), for example based on synchronization-facilitating data that originate from in-vivo device 210. Operation of MMU 240 may be synchronized to the operation of LSS 230 also to ensure that MMU 240 generates an orientation correction signal 242 that may be based or depend on, or derived from, up-to-date orientation data. Processor 224 may send a synchronization signal 244 to MMU 240 and synchronization signal 228 to LSS 230 in order to synchronize between MMU 240, LSS 230, and in-vivo device 210. Processor 224 may use orientation data embedded in, for example, localization data 229 that LDU 226 outputs to detect the instantaneous orientation of in-vivo device 210, and transfer (246) a movement signal to MMU 240, to cause MMU 240 to generate a magnetic field (242) to move in-vivo device 210 in a direction that coincides, matches or complies with the instantaneous spatial orientation of in-vivo device, as defined by the spatial direction of the in-vivo device's longitudinal axis. An in-vivo device 210 may also include a magnetic thrust unit ("MTU") 213. MTU 213, in conjunction with magnetic field 242, may generate/produce or induce magnetic thrusting force that can push/propel in-vivo device 210 forwards. ('Forwards' means in a direction pointed at by the steerable/guided head/end of the in-vivo device.)

FIG. 3 shows an in-vivo imaging system 300 according to an example embodiment. While FIG. 2 references an in-vivo device (in-vivo device 210) that transmits data frames that may be related to or include any type of sensory data (e.g., pH data), FIG. 3 shows in-vivo device 310 with an imager as an example sensor, in which case in-vivo device 310 may be referred to as an "in-vivo imaging device" or an "in-vivo imager", and frames transmitted by or from in-vivo device 310 may be referred to as "image frames" (although image frames may include also other types of data, including localization (e.g., orientation and/or location) data and/or other types of sensory data).

In-vivo imaging system 300 may include in-vivo imager 310, data recorder 320, a user workstation 330, which may be, for example, a workstation or personal computer, and a display 303 for displaying, for example, images and/or a video clip or moving image stream which is produced from images, and for displaying the spatial orientation (and in some embodiments also the location) of the in-vivo device, etc. (The spatial orientation and magnitude of the thrust force acting on in-vivo device 310 may also be displayed on display 303.)

An in-vivo imaging device may have one or more imagers. By way of example, in-vivo imager 310 includes one imager (e.g., imager 312) (numbers of imagers other than one or two may be used). In-vivo imager 310 may also include a light/illumination source 314 for illuminating a GI section to be imaged, a frame generator 320 for producing an image frame for captured images, a controller 360, a storage unit 340 for storing data, a transmitter or transceiver 350 for transmitting images frames and, optionally, for receiving data and/or commands from data recorder 320, and an electrical power source 301 for powering these components and circuits. Power source 301 may include a charge storing device (e.g., one or more batteries, which may be rechargeable or not) with an electrical circuit that jointly facilitates transfer of electrical power from an external power source to the in-vivo device through electromagnetic induction.

Transmitter 350 may transmit, within a work cycle of in-vivo device 310, a data frame to a receiver (e.g., data recorder 320). Controller 360 may be configured, within the work cycle, to operate a LSU 302 to sense localization signal(s), and to transmit data representative of the sensed localization signal(s) during the same work cycle or during a subsequent work cycle. A work cycle may be a repeating period of time during which certain operations may occur, for example, during sub-portions of the work cycle. LSU 302 may include an orientation sensor similar to orientation sensor 212A and, optionally, also a location sensor similar to location sensor 212B and, thus, it may function in a similar way as LSU 212.

In-vivo imager 310 may include a location and steering circuit 372. LSU 372 may include LSU 302 for sensing localization signals generated, for example, by LSS 230 of FIG. 2. LSU 372 may also include a magnets thrust unit (MTU) 311 to facilitate thrusting/propelling of in-vivo imager 310, for example through interaction with magnetic fields which may be generated by a maneuvering system similar to MMU 240 of FIG. 2. Data representing or derived from the EMF signals induced in LSU 302 may be transmitted, for example, to data recorder 320 by embedding the data in image frames and/or by using frames that may be dedicated to (e.g., selected to) transfer such data.

At the time of, or shortly after, imaging device 310 is swallowed or otherwise inserted, or after some predetermined delay (e.g., 2 minutes), imager 312 may start capturing images of areas of the GI system. Typically, the exposure time of imager 312 is 2-3 milliseconds, though this may change according to the application. Imager 312 may include an image sensor that may be, or include, an array of photo sensor elements (e.g., pixels) such as 256×256, 320× 320, 1 Mega pixel or any other suitable array. Imager 312 outputs image data 313 by using a pixel format corresponding to the used pixels. An image data may represent, for example, a captured image and, optionally, additional selected portions thereof, for example a decimated image.

Frames generator 320 may receive image data 313 that represents a captured image, and produce a corresponding image frame (or "frame" for short) that contains image data 313. A frame typically includes a header field that contains information and/or metadata related to the frame itself (e.g., information identifying the frame, the serial number of the frame, the time the frame, the bit-wise length of the frame, etc.), and a payload field. The payload may include an uncompressed version of the image data and/or a compressed version thereof, and a decimated image. The payload may also include additional information, for example information related to the output signals of sensing coils, or other electromagnetic field detectors, of LSU 302.

Controller 360 may controllably operate, among other things, illumination/light source 314 to illuminate areas traversed by in-vivo imager 310, and schedule the images capturing times accordingly. Controller 360 may use time specifics, which may be stored in storage unit 340, to time the operation of illumination source 314 to illuminate, for example, four times per second (or faster) to enable capturing four images (or more than four images) per second, and the operation of transceiver 350 to concurrently transmit corresponding frames at the same rate or at a different rate. Controller 360 may operate illumination source 314 to capture more images per second, for example seventeen images per second, and transceiver 350 to concurrently transmit corresponding frames at the same rate or at a different rate. Controller 360 may temporarily store captured images and related image frames in data storage unit 340. Controller 360 may also perform various calculations and store interim calculation results in data storage unit 340. Controller 360 may also time the operation of LSU 302 (e.g., LSU 302 readout from which the orientation, and in some embodiments also the location, of in-vivo imager 310 may be deduced; e.g., internally by controller 360, or by an external system; e.g., data recorder 320). Controller 360 may also time the writing (e.g., adding, appending, or otherwise embedding) of localization data (e.g., the sensing coils readout and/or a manipulated version thereof) into the corresponding frame; e.g., into a frame that is to be transmitted, for example, immediately after the output of the sensing coils is read. After frames generator 320 produces a frame for a currently captured image and embeds localization data into the frame, controller 360 may use transceiver 350 to wirelessly transfer 342 the frame to data recorder 320. Data recorder 320 may be worn by the person whose GI system is to be imaged. Controller 360, by executing software or instructions, may carry out steps which are performed by frame generator 320, and other functions in in-vivo device 310, and thus may function as this/these units.

Data recorder 320 may include a receiver or transceiver 222, a frame parser 370, and a processor 224 for managing them. Data recorder 320 may include additional components (e.g., USB interface, Secure Digital ("SD") card driver/interface, controllers, etc.), elements or units for communicating with (e.g., transferring data frames, exchanging data, etc.) a processing and/or displaying systems that may be configured to process images and localization data originating from in-vivo imager 210, and related data. Transceiver 222 may receive a data frame corresponding to a particular captured image, and frame parser 370 may parse the data frame to extract the various data contained therein (e.g., image data, decimated image associated with the particular captured image, localization data, etc.). In some embodiments, some data frames, which are referred to herein as "localization frames", may be dedicated to contain and transfer only or mostly localization data. Localization frames may, for example, include localization data (e.g., only orientation data, or only location data, or both types of data) but not image data. Using localization frames in addition to image frames that include localization data may enable reading the localization data (e.g., the output of LSU 302) at a rate that may be higher than the images capturing rate. For example, n (n being an integer) localization frames may be interposed (e.g., 'inserted' between, in time sequence), for example, between image frames, to form therewith a stream of frames.

LDU 326 may function in the same way as LDU 226 of FIG. 2. LDU 326 may receive localization data from frame parser 370, extract therefrom orientation information related to the instantaneous spatial orientation of in-vivo device 210, and output (328) the orientation information to orientation-to-electromagnetic field converter ("OEMC") 380. OEMC 380 may receive the orientation information and output a control signal as a function of, or in response to, the orientation information. For example, OEMC 380 may use the orientation information to calculate magnetic parameters (e.g., magnetic gradient) for a magnetic maneuvering system generating a maneuvering magnetic field such that the magnetic field, when generated, in conjunction with MTU 311, would generate a magnetic gradient for inducing a magnetic thrust force whose spatial orientation coincides with the spatial (3-D) orientation of the in-vivo device. OEMC 380 may, then, output (382) the control signal to the magnetic maneuvering system. OEMC 380 may be regarded as converting the orientation information to a control signal that controls the magnetic maneuvering system that generates the maneuvering magnetic field.

Data recorder 320 may transfer the control signal (382) to a magnetic maneuvering unit similar to MMU 240 of FIG. 2, or to a similar magnetic maneuvering system, in order to cause the magnetic maneuvering system to generate the electromagnetic field in order to produce or induce the magnetic thrust force required to push, thrust or propel the in-vivo device in the direction of the spatial orientation of the in-vivo device. OEMC 380 may be a separate subsystem, or circuit, or it may be integrated into LDU 328. Processor 224, by executing software or instructions, may carry out steps which are performed by any of LDU 326 and OEMC 380, and other functions in data recorder 320, and thus may function as these units. Either or both of processors 224 and 305 may be configured to carry out all or parts of embodiments of the present invention by for example executing software or instructions for example in a memory.

User workstation 330 may include a display or be functionally connected to one or more external displays, for example to display 303. Workstation 330 may receive frames (e.g., image frames, localization frames, etc.), images and/or orientation information from data recorder 320, and present them in real-time, for example as live video, or produce a video stream that also contains location and orientation information that may also be displayed on, for example, display 303. Workstation 330 may include a memory (e.g., memory 304) for storing the frames and orientation information transferred from data recorder 320, and possibly related metadata, and a processor (e.g., processor 305) for processing the stored frames and other data. Workstation 330 may display selected images, or a video clip (e.g., a moving image stream) compiled from such images, and orientation information pertaining to, or representing, the instantaneous orientation of the in-vivo device and/or the instantaneous spatial direction of the magnetic thrust force acting on MTU 311 of the in-vivo device, e.g., to a human operator, health care person, physician, etc.

FIG. 4 depicts a method for navigating an in-vivo device by the GI tract according to an embodiment of the invention. (Assume that an in-vivo device has been swallowed by a subject.) The method may be applicable to an in-vivo device comprising a magnetic thrust end and a steerable/guidable end/head opposite (e.g., along a/the longitudinal axis of the in-vivo device) to and spaced apart from the magnetic thrust end and steerable by a wall of the gastrointestinal tract, the magnetic thrust end comprising a magnetic thrust unit. By "spaced apart" is meant one end (e.g., magnetic thrust end) being on, or located at, one side of a/the center of mass of the in-vivo device (e.g., center of mass 152, FIG. 1A), and the other end (e.g., magnetic thrust end) being on, or located at, another side of a/the center of mass of the in-vivo device (e.g., center of mass 152, FIG. 1A).

At step 410, the spatial orientation (a three-dimensional (3-D) orientation) of the in-vivo device (e.g., in-vivo device 100, FIG. 1) in the GI tract of the subject (e.g., GI tract 102, FIG. 1) may be determined, for example, after sensing localization signals (which may be generated by a system similar to LSS 230 of FIG. 2) by using a LSU similar to LSU 212 of FIG. 2, or LSU 302 of FIG. 3 (e.g., by an orientation sensor included in the LSU; e.g., by orientation sensor 212A). (Other methods for determining the orientation of the in-vivo device may be used. For example, one such method may not require that an electromagnetic detector be included in the in-vivo device.) At step 420, the in-vivo device may be moved in the GI tract by applying a magnetic force cycle, the magnetic force cycle may include a time period during which a magnetic thrust force may be applied to (induce in) the magnetic thrust unit in order, or so as, to move the in-vivo device in a direction coinciding with the determined orientation of the in-vivo device. Steps 410 and 420 may be reiterated (430) in order to move the in-vivo device further, or farther.

Application of the magnetic thrust force to the magnetic thrust unit may be concurrent to the determination of the orientation of the in-vivo device. Determination of the orientation of the in-vivo device and application of the magnetic thrust force may be performed at different times. The orientation of the in-vivo device may be determined n times per second. If a series of magnetic thrust force activations is applied to the magnetic thrust unit, the orientation of the in-vivo device may be determined n times between successive magnetic thrust force activations. The magnetic thrust force may be applied to the magnetic thrust unit constantly or continually between successive determinations of the orientation of the in-vivo device. The magnetic thrust force may be applied to the magnetic thrust unit n times or intermittently between successive determinations of the orientation of the in-vivo device.

FIG. 5 depicts a method for navigating an in-vivo device according to another embodiment of the invention. (Assume that an in-vivo device has been swallowed by a patient.) At step 510, the in-vivo device may use an orientation sensor (e.g., orientation sensor 212A) to sense localization signals, from which at least the spatial orientation of the in-vivo device may be determined, calculated or inferred, at step 520, either internally (by the in-vivo device), or by an external system; e.g., data recorder, to which the in-vivo device may transfer the sensed localization signals. Sensing of the localization signals may be implemented by using, for example, LSU 212 of FIG. 2, or by LSU 302 of FIG. 3. Determining, calculating or inferring/deducing the orientation of the in-vivo device in the GI tract from the sensed signals may be done, for example, by processor 224 of FIGS. 2 and 3, or by controller 360 of FIG. 3.

At step 530, magnetic characteristics of a magnetic field may be calculated based on the determined, calculated or inferred/deduced spatial orientation of the in-vivo device such that a magnetic thrust force induced in, or generated jointly with, a magnetic thrust unit (MTU) of, or used by the in-vivo device, may be applied to the in-vivo device in a direction coinciding with the in-vivo device's determined, calculated or inferred/deduced orientation. At step 540, the magnetic field may be generated using the calculated magnetic characteristics, to apply the magnetic force to the MTU, hence to the in-vivo device. The magnetic characteristics of the magnetic field may be calculated, or otherwise determined, for example, by any one of processor 224, LDU 226, LDU 326, and MMU 240.

At step 550, the orientation of the in-vivo device may be rechecked (determined, calculated or inferred/deduced again; e.g., by performing steps similar or identical to steps 510 and 520), and at step 560 it is checked whether the spatial orientation sensed (and determined, calculated or inferred/deduced) at step 550 indicates a change in the spatial orientation of the in-vivo device with respect to the previously determined, calculated or inferred/deduced spatial orientation. If there is no change in the orientation of the in-vivo device (the decision shown as 'No' at step 560), the same magnetic thrust force (e.g., a force having the same orientation) may be used to push/thrust the in-vivo device further, in that same direction. Therefore, steps 540 and 550 (loop 570) may be reused or iterated through. (The magnetic field for applying, producing or facilitating the magnetic force may be generated by a magnetic system similar to MMU 240 of FIG. 2.) However, if there is a change in the orientation of the in-vivo device (the decision shown as 'Yes' at step 560), a new magnetic thrust force is generated, with a spatial orientation that complies with the new/updated orientation of the in-vivo device. New magnetic parameters may be calculated, at step 530, in order to generate a magnetic field that produces the new force. Loop 580 may be repeated whenever the spatial orientation of the in-vivo device changes. Otherwise, the same magnetic force may be applied to the in-vivo device, continually, constantly or intermittently, for as long as the in-vivo device's orientation remains unchanged. (By the 'same magnetic force' is meant magnetic force with the same orientation, and, optionally, with the same magnitude, though in some embodiments the magnitude of the force may be controlled; e.g., separately and either dependently or independently of the orientation/direction of the force.) In other embodiments, the magnetic force's magnitude may depend on the orientation of the magnetic force. For example, an in-vivo device ascending in the GI tract may require a stronger force in order to counteract or overcome gravity force.) A decision regarding whether the orientation of the in-vivo device has changed, as per step 560, may be made by, for example, processor 224 or controller 360.

Figure 6:
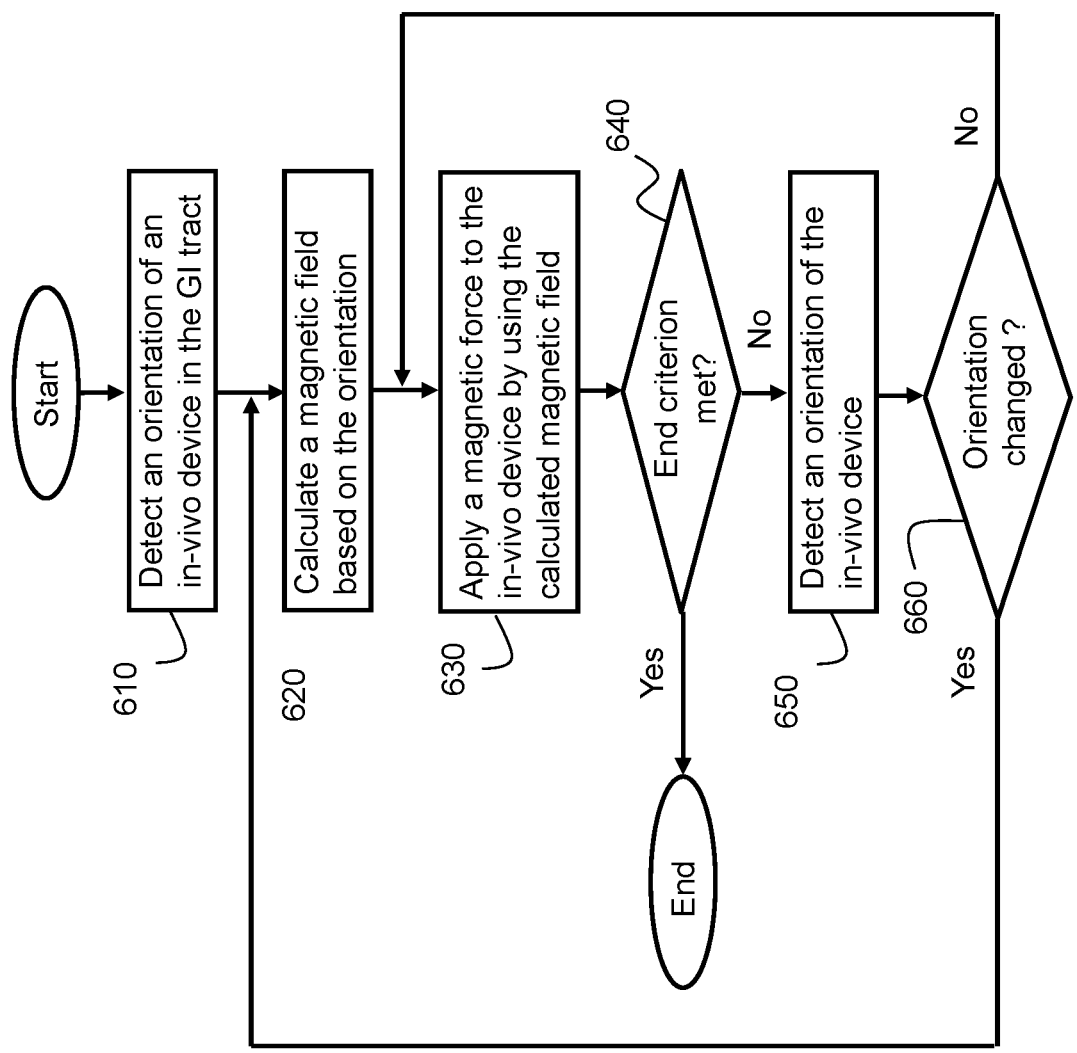
FIG. 6 depicts a method for navigating an in-vivo device according to yet another embodiment of the invention.

FIG. 6 depicts a method for navigating an in-vivo device according to yet another embodiment of the invention. (Assume that an in-vivo device has been swallowed by a patient.) At step 610, a spatial orientation of the in-vivo device in the GI tract may be detected. At step 620, magnetic parameters of a magnetic field may be calculated based on (in accordance with) the detected orientation.

At step 630, a magnetic thrust force having an orientation complying with the detected device's orientation may be applied to the in-vivo device (for example to a magnetic thrust unit (MTU) included in the in-vivo device) by generating a magnetic field whose magnetic field parameters are the ones calculated at step 620. The magnetic thrust force may be applied to the in-vivo device momentarily or recurrently, while, after each occurrence, a navigation ending criterion ("NEC") may be checked in order to determine whether the magnetic field generating system (e.g., MMU 240) should be brought to a halt or to an idle state, for example, to let the in-vivo device be propelled only by natural peristaltic. Reaching a certain location in the GI tract (e.g., stomach), or a certain amount of time (e.g., 2 hours) elapsing from a reference time, are examples of navigation ending criteria.

At step 640, it is checked whether, after application of the magnetic thrust force on the in-vivo device at step 630 a predefined ending criterion is met. If the ending criterion is met (this is shown as "Yes" at step 640), the in-vivo device navigation procedure may be terminated (e.g., the magnetic force stopped/removed). However, if the NEC is not met (this is shown as "No" at step 640), the spatial orientation of the in-vivo device is rechecked after application of the magnetic force at step 630. At step 660, it is checked whether the orientation rechecked at step 650 differs from the previously detected orientation (the orientation detected at step 610). If the orientation rechecked at step 650 does not differ from the previously detected orientation (this condition is shown as "No" at step 660), the same magnetic thrust force may be used. However, if the orientation rechecked at step 650 differs from the previously detected orientation (this condition is shown as "Yes" at step 660), parameters of the magnetic field may be recalculated in order to impart to the MTF (a 3-D vector) propelling/thrusting the in-vivo device at step 630 a new direction that coincides with, or matches that of, the new orientation of the in-vivo device.

Figure 7B:
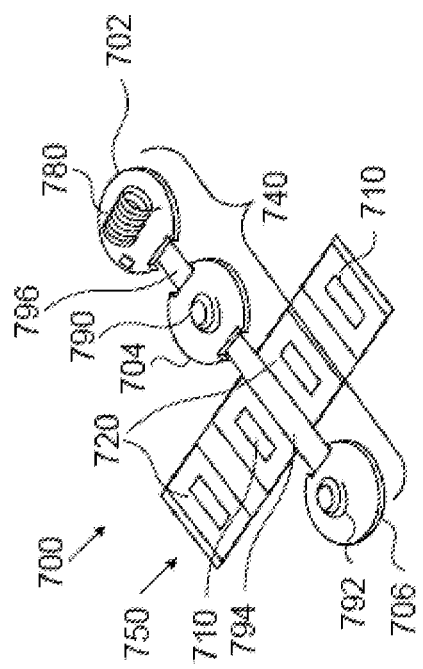
FIGS. 7A and 7B depict an example printed circuit board ("PCB") of an in-vivo device that includes an orientation sensor for sensing localization signals.
Figure 7A:
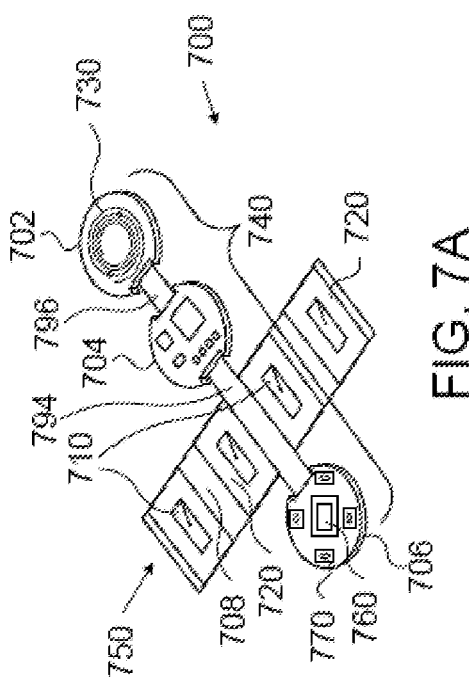

FIGS. 7A and 7B depict an example printed circuit board ("PCB") of an in-vivo device that is configured to sense localization signals. (The in-vivo device subject of FIGS. 7A-7D may also include a MTU similar to, for example, MTU 213 of FIG. 2, or MTU 302 of FIG. 3, although this is not shown in FIGS. 7A-7D.) FIG. 7A depicts an example cross-like multilayered imaging and sensing printed circuit board (MISP) 700 of an in-vivo device similar to, for example, in-vivo imaging device 210. MISP 700 may include 1-layer portions or sections even though it is generally referred to as a 'multilayered' PCB. MISP 700 may be rigid-flex, which means that portions, parts or sections thereof may be rigid whereas other portions, parts or sections thereof may be flexible enough to allow them to be folded into a cylinder-like structure. MISP 700 may be full-flex, which means that all of its portions/parts/sections are flexible. By way of example, MISP 700 is shown including two printed circuit board ("PCB") branches that 'cross', or intersect, each other: an imager section 740 and a localization sensing unit (LSU) 750.

Imager section 740 includes at least imaging circuitry 760, for which reason section 740 is referred to as 'imager section'. Imager section 740 may include, for example, three rigid sections, designated as 702, 704 and 706, that may be multilayered, and two flexible sections, designated as 794 and 796, that may also be multilayered. Flexible section 794 may connect rigid sections/portions 704 and 706 and be partly sandwiched between layers of these sections/portions. Section 796 may connect rigid sections 702 and 704 and be partly sandwiched between layers of these sections. The other side of sections 702, 704, and 706 may also accommodate additional elements and/or components, as depicted in FIG. 7B.

Imaging circuit 760, which may include an imager similar to imager 312 of imaging device 310, may be mounted, for example, on rigid section 706. An illumination source similar to light source 314 of in-vivo device 310 may also be mounted on rigid section 706, as shown, for example, at 770. By way of example, the illumination source mounted on rigid section 706 includes four light sources which are equidistantly and circle-wise positioned on rigid section 706. Other electronic components of the in-vivo device (e.g., ASIC, controller, transmitter, crystal oscillator, memory, etc.) may be mounted, for example, on section 704 and/or on section 702.

LSU 750 includes sensing coils for sensing (localization) magnetic fields by which the location and/or orientation of the in-vivo device may be determined. By way of example, LSU 750 includes electromagnetic sensing coil 710 and electromagnetic sensing coil 720. Electromagnetic sensing coils 710 and 720 are shown to be rectangular, but they need not be rectangular. The two sensing coils 710 are collectively referred to as sensing coil 710 because the two sensing coils 710 may be electrically interconnected to functionally form one electrical component (i.e., one sensing coil). Likewise, the two coils 720 are collectively referred to as sensing coil 720 because the two coils 720 may be electrically interconnected to functionally form one sensing coil. An additional sensing coil, which may functionally be part of LSU 750, may be mounted on, or be embedded, incorporated into, built into or formed in rigid section 702 (the additional sensing coil is shown at 730). LSU 750 may be multilayered to accommodate sensing coils of enlarged inductance to increase the electromagnetic fields sensing sensitivity.

Figure 7D:
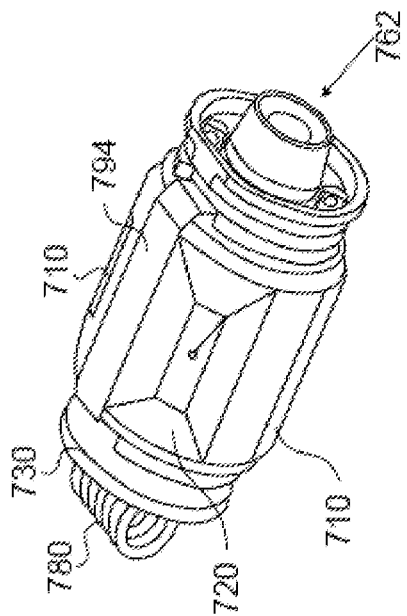
FIG. 7D shows the partly assembled in-vivo device of FIG. 7C with an optical head mounted on top of a rigid section.

Flexible multilayered PCB dielectric substrate 708 may accommodate sensing coils 710 and 720. Each PCB layer of multilayered PCB substrate 708 may accommodate some of the coil turns of sensing coils 710 and/or some of the coil turns of sensing coils 720. LSU 750 is shown in FIGS. 7A and 7B outspread. Cylindrically folding LSU 750 places some turns of sensing coils 710 against/opposite other turns of sensing coils 710 (as shown in FIG. 7D) such that their normal lines substantially coincide with a same axis (e.g., 'X' axis of the X-Y-Z coordinates system), and some turns of sensing coils 720 against/opposite other turns of sensing coils 720 such that their normal lines substantially coincide with another same axis (e.g., 'Y' axis of the X-Y-Z coordinates system). (The opposing sensing coil 720 is hidden in FIG. 7D, and the planes of sensing coils 720, though curved a little, are generally perpendicular to the planes of sensing coils 710.)

FIG. 7B shows the other side of MISP 700. By way of example, section 702 accommodates an antenna 780 to facilitate radio frequency (RF) communication between the in-vivo imaging device and the data recorder or receiver with which the in-vivo imaging device operates; and sections 704 and 706 respectively accommodate electrical springs 790 and 792.

Figure 7C:
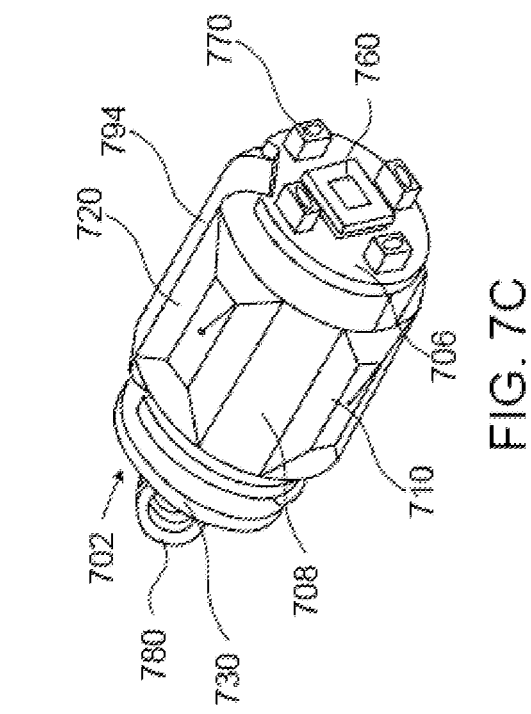
FIG. 7C shows a partly assembled in-vivo imaging device, with the imaging section folded/introverted and with localization sensing unit cylindrically folded.

Imaging section 740 is shown in FIGS. 7A and 7B outspread, but, to facilitate assembling of the in-vivo device, it is made foldable such that the rigid sections thereof may be stacked in a parallel manner such that rigid sections 704 and 706 may hold there between one or more batteries while the lines normal to the planes of sections 704 and 706 coincide with a longitudinal axis of the in-vivo imaging device. When rigid sections 704 and 706 are folded, electrical springs 790 and 792 secure the one or more batteries in place, and electrically connect them to the imaging device's electrical circuit (e.g., to MISP 700). FIG. 7C shows a partly assembled in-vivo imaging device, with the imaging section 740 folded/introverted and the LSU 750 cylindrically folded. FIG. 7D shows the partly assembled in-vivo device of FIG. 7C with an optical head 762 mounted on top of rigid section 706.

As described herein, information regarding velocity of the in-vivo device may be used as a basis for the application of a magnetic thrust force that thrusts or propels an in-vivo device in the GI tract. Application of the magnetic thrust force may include changing, over time (e.g., across subsequent activations of the magnetic force), the magnitude of the magnetic force (as per the example of FIG. 8), or period of the magnetic force (e.g., duty cycle; e.g., as per the example of FIG. 9), or both period and magnitude of the magnetic thrust force. Due, in part, to different regions of the GI system having different peristaltic characteristics, an in-vivo device is expected to travel in the GI tract at a certain speed or velocity that depends on the location of the in-vivo device in the GI tract. A priori information regarding expected or desired velocity of an in-vivo device may be used to control the magnitude and/or period of the magnetic thrust force that is applied to the in-vivo device (in order to reach or maintain the expected, or desired, velocity).

FIG. 8 depicts an example timing diagram 800 according to some embodiments of the invention. By way of example, timing diagram 800 depicts five consecutive magnetic force cycles ("MFCs") respectively corresponding to five magnetic force activations ("MFAs"), designated as MFA 810, MFA 820, MFA 830, MFA 840 and MFA 850. In some embodiments, each MFA may occur using the same (activation) cycle length, which is referred to herein as 'magnetic force cycle' (MFC), and the same duty cycle. (Each of MFAs 810-850 is shown having the same period, T, within the same cycle, MFC). By way of example, FIG. 8 depicts only five MFCs that may be part of a long series of MFCs, where each MFC may include a magnetic force activation (MFA) period (e.g., MFAs 810-850) during which MTF is applied to (induced in) the MTU of the in-vivo device to thrust the in-vivo device, and an orientation settling period (e.g., orientation settling period 812 and 822. Other MFCs also have their respective orientation settling period) during which no MIT is applied to (induced in) the MTU, or only a relatively low MIT may be applied to (induced in) the MTU, in order to let the GI wall 'easily' reorient the in-vivo device. In the example diagram depicted in FIG. 8, the MFA periods are identical, as are the orientation settling periods.

If the velocity of the in-vivo device in a particular GI region or portion is lower than a reference value (the in-vivo device is moving slower than, for example, expected or desired), a parameter of the magnetic thrust force may controllably be changed to change that. For example, the magnitude of the MFC (an example MFC's parameter) may be increased temporarily or momentarily, for example during the next n magnetic force activations (MFAs) (e.g., 4 activations), and vice versa if the device's actual velocity is faster than the reference value/velocity; e.g., if the in-vivo device moves faster than expected or desired. Referring to FIG. 8, there are two initial, or basic, magnetic force activations (MFAs) 810 and 820, each having a an initial, or basic, magnitude M1, which may be relatively low (e.g., less than or equal to 20 gram force), and the same duration (T). (Assume that at time t1 it is determined that the velocity of the in-vivo device is lower than expected or desired.) At time t1 (or later but before the subsequent MFA; e.g., before MFA 830 is due), the MFA may controllably be changed (e.g., by a processor similar to processor 224 of FIG. 2, or controller 360 of FIG. 3) such that its magnitude (e.g., the magnitude of MFA 830) is M2 (M2>M1).

During the next MFC or MFA (e.g., MFA 840), between times t2 and t3, the magnitude of MFA 840 may, in some embodiments, stay at level M2, or, in other embodiments, it may be higher; e.g., be at or changed to level M3 (M3>M2>M1). MFAs with magnitude(s) higher than the initial or basic level/value (e.g., M1) may be maintained until the velocity of the in-vivo device increases to an/the expected or desired value. For example, if by time t3 (for example) the corrective measure taken (using magnetic force with increased magnitude) is proved helpful, it may be determined that the magnitude of the magnetic force to be applied during the subsequent MFA (e.g., MFA 850) should resume the initial or basic magnitude, M1. (If it turns out that the velocity of the in-vivo device is higher than expected or desired, the control process described above may be reversed; e.g., the magnitude of the magnetic force during one or more MFCs may be set to a value that is lower than M1, or to zero; i.e., it may be removed, stopped or nulled altogether.) As shown in FIG. 8 and described herein, the duty cycle is maintained in each MFC. Increasing and decreasing the magnitude of the magnetic force may be gradual or in steps (stepwise). The value of the MTF may be changed, adjusted or modified (increased or decreased) linearly, gradually, or at steps (step wised) across subsequent MFAs, and the increasing (or decreasing, as the case may be) slope or the size of the step may be a function of the velocity error (e.g., deviation of the actual velocity of the in-vivo device from the expected or desired velocity).

A processor similar to processor 224 of FIG. 3 or a controller similar to controller 360 of FIG. 3 may determine whether a magnitude of a magnetic force should be changed during specific or some magnetic force activations (MFAs), and, if it should, to what value, and using which slope or step size. Alternatively, a magnetic maneuvering unit similar to MMU 240 may take on the aforesaid determination.

The problem caused by the stabilizing effect of the stabilizing torque generated/produced by the thrusting magnetic field may be solved or mitigated by, for example, applying the thrusting/propelling magnetic force in pulses, as shown at 802, using a thrust-and-settle mode that may include thrusting the in-vivo device momentarily, then letting the device's orientation to settle, then thrusting the in-vivo device momentarily again, and so on. For example, during the first MFC, activation 810 of the magnetic force is limited to period T, then the magnetic force is deactivated for a time period 812 ('settle time') during which the stabilizing torque may be nullified or minimized in order to enable the in-vivo device's orientation to freely change only by the turning torque that is exerted by the wall of the GI tract. (That is, nullifying, or minimizing, the stabilizing torque enables the device's guidable end/head to be easily guided/steered by the GI's wall.) Then, during the second MFC, activation 820 of the magnetic force is (in this example it is also) limited to period T, then the magnetic force is deactivated for a time period ('settle time') 822, during which the stabilizing torque may be nullified or minimized in order to enable the in-vivo device's orientation to freely change only by the turning torque exerted by the wall of the GI tract, and so on, letting the in-vivo device's orientation to settle (e.g., to the orientation enforced only by the wall of the GI tract) in-between each two consecutive activations (pulses/bursts) of thrusting/propelling magnetic force.

FIG. 9 depicts a timing diagram 900 according to other embodiments of the invention. If the velocity of the in-vivo device in a particular GI region or portion is lower than a reference value (the in-vivo device is moving slower than, for example, expected or desired), a parameter of the MTF may controllably be changed to change that. For example, the duty cycle of the MFC (an example MFC's parameter) may be increased temporarily or momentarily, for example during the next n magnetic force activations (MFAs) (e.g., 5 activations), and vice versa if the device's actual velocity is higher than the reference value/velocity; e.g., if the in-vivo device moves faster than expected or desired. By way of example, timing diagram 900 shows five MFCs (MFC-1, MFC-2, MFC-3, MFC-4, MFC-5) respectively corresponding to five consecutive magnetic force activations (MFAs), designated as MFA 910, MFA 920, MFA 930, MFA 940 and MFA 950. In some embodiments, each MFA occurs using the same magnetic force cycle (MFC) and a constant magnitude (M). In other embodiments, the magnitude of the magnetic thrust force may change in addition to a change in the duty cycle. Some of MFAs 910-950 are shown having different periods (temporal widths) embodying different duty cycles. By way of example, FIG. 9 depicts only five MFCs that may be part of a long series of MFCs, where each MFC may include a magnetic force activation (MFA) period (e.g., MFAs 910-950) during which MTF is applied to (induced in) the MTU of the in-vivo device to thrust the in-vivo device, and an orientation settling period (e.g., orientation settling period 912, 922 and 932. Other MFCs also have their respective orientation settling period) during which no MTF is applied to (e.g., induced in) the MTU, or only a relatively low MTF may be applied to (e.g., induced in) the MTU, in order to let the GI wall easily reorient the in-vivo device. In the example diagram depicted in FIG. 9, the MFA periods may vary across MFCs, as are the orientation settling periods.

FIG. 9 depicts two initial, or basic, magnetic force cycles (MFC-1 and MFC-2) with respective magnetic force activations (MFAs) 910 and 920 that may have the same initial, or basic, magnitude, M, that may be; e.g., less than or equal to 20 gram force. A magnetic force having the initial, or basic, magnitude, M, may be associated with an expected or desired velocity of an in-vivo device. In addition, MFAs 910 and 920 may have a same initial, or basic, duty cycle, having the same duration (T1). It is assumed that by time t1 it is determined that the velocity of the in-vivo device is lower than the expected or desired value. Consequently, it may be decided to increase the duty cycle of the subsequent MFA (e.g., MFA 930) from, say, approximately 30% in MFC-1 and MFC-2 (T1/(T1+T0)≈30%) to approximately 50% in MFC-3 (T2>T1). If increasing the duty cycle in MFC-3 does not increase the velocity of the in-vivo sufficiently (e.g., to the expected or desired value) or at all, the duty cycle can be further increased; e.g., to approximately 60% in the subsequent MFC (e.g., MFC-4, T3>T2>T1) and, then (if still required) to; e.g., approximately 90% in the subsequent MFC (e.g., MFC-5, T4>T3>T2>T1), etc. When the velocity is increased to the designated value, be it an expected value or desired value, the duty cycle of the consecutive MFCs may be reduced; e.g., back to the initial, or basic, value, as is the case with MFC-1 and MFC-2. Increasing and decreasing the duty cycle of magnetic force cycles may be gradual or in steps (stepwise).

A processor similar to processor 224 of FIG. 3 or a controller similar to controller 360 of FIG. 3 may determine whether a duty cycle of a magnetic force cycle (MFC) should be changed for specific or some magnetic force activations (MFAs), and, if it should, to what value and using which slope or step size. Alternatively, a magnetic maneuvering unit similar to MMU 240 may take on the aforesaid determination.

Some embodiments may include changing, or manipulating, the magnitude of the magnetic force across consecutive MFCs, as well as the duty cycle of at least some of the MFCs. For example, it may be decided (e.g., by a processor similar to processor 224 of FIG. 3 or a controller similar to controller 360 of FIG. 3) that the magnitude of the magnetic force during a particular MFC should be changed (increased or decreased), and that the duty cycle of that particular MFC should also be changed/varied (increased or decreased). Increasing the magnitude of the magnetic force and, at the same time, extending the time length during which that magnitude is effected (increasing also the associated duty cycle) is beneficial in cases where a fast velocity response is required; e.g., where a velocity of an in-vivo device is very low and it is required to reach a higher velocity fast. (A reverse effect can be obtained by decreasing the magnitude of the magnetic force and the duty cycle at the same time.) The duration or period of the magnetic (thrust) force (e.g., duty cycle of the MFCs) may be changed, adjusted or modified (increased or decreased) linearly, gradually, or at steps (step wised) across subsequent MFCs, and the increasing (or decreasing, as the case may be) slope or the step may be a function of the velocity error (e.g., deviation of the actual velocity of the in-vivo device from the expected or desired velocity).

Figure 10:
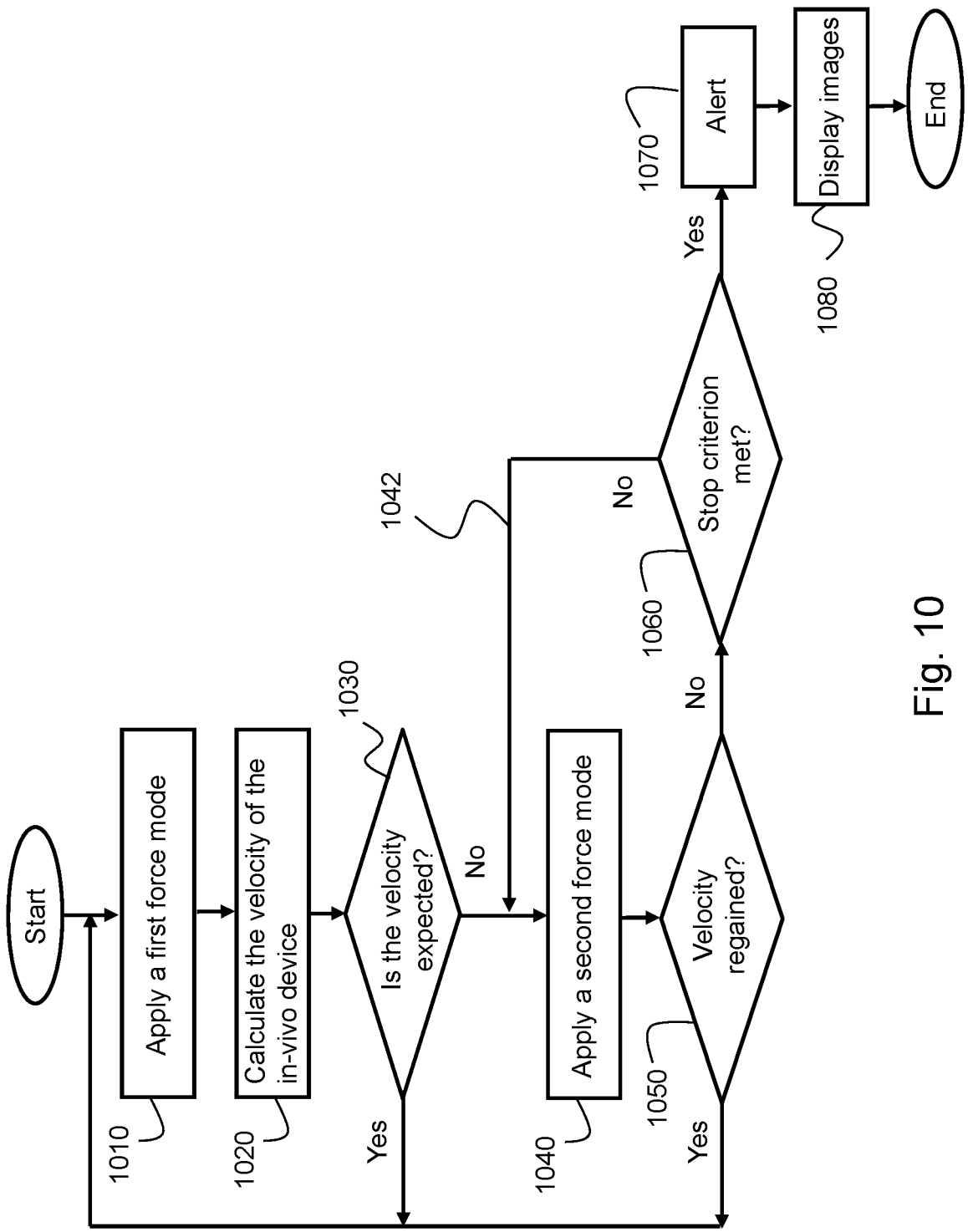
FIG. 10 depicts a method for velocity-dependent navigation of an in-vivo device according to an embodiment of the invention.

FIG. 10 depicts a method for velocity-dependent navigation of an in-vivo device according to an embodiment of the invention. At step 1010, a first force mode may be applied to an in-vivo device while the in-vivo device is in, or moves or advances through, some portion or region of the GI tract, for example through the small intestine. The first force mode may be an initial, or basic, mode of operation during which a magnetic force applied to an in-vivo device may have a 'moderate' magnitude (e.g., approximately 20 gr. force, or so) that may suffice to subtly, or smoothly, move the in-vivo device in a desired, or expected, velocity that may depend, for example, on the GI region the in-vivo device is in.

At step 1020, the velocity of the in-vivo device may be calculated, for example, from location information that may be collected while the in-vivo device moves through the GI tract, and, at step 1030, it is checked whether the calculated velocity is the expected velocity or desired velocity. If it is determined that the calculated velocity is the expected or desired velocity (the condition is shown as "Yes" at step 1030), the same (first) force mode may still be used (e.g., step 1010 may be reiterated). However, if it is determined that the calculated velocity is neither the expected velocity nor the desired velocity (the condition is shown as "No" at step 1030), a second force mode may operationally replace the first force mode, as per step 1040. Characteristics of the second force mode may be set based on whether the calculated velocity is greater or smaller than the expected or desired velocity. For example, the magnitude of the magnetic force and/or the duty cycle of the magnetic force cycle (MFC) may be manipulated, for example, as described in connection with FIGS. 8 and 9.

At step 1050, it is checked whether the expected or desired velocity of the in-vivo device is regained (within an acceptable margin or dissimilarity) as a result of the application of the second force mode. If the device's expected or desired velocity is regained (the condition is shown as "Yes" at step 1050), the same (first) force mode may still be used (e.g., step 1010 may be revisited). However, if it is determined that the calculated velocity is not the expected, or desired, velocity (the condition is shown as "No" at step 1050), a stop criteria may be checked at step 1060. If the stop criteria is not met (the condition is shown as "No" at step 1060), the second force mode may still be active (e.g., step 1040 may be reiterated) because it may take several iterations (1042) to regain the expected, or desired, velocity. However, if the stop criteria is met (the condition is shown as "Yes" at step 1060), this may mean that the in-vivo device may be stationary, or that the second force mode is unsuitable for regaining the expected or desired velocity. Therefore, an alert may be presented to a user, at step 1070, audibly or visually, or both audibly and visually, and, at step 1080, concurrently display real-time images to the use, so the user can assess the location of the in-vivo device in the GI system, as well as the reason why the in-vivo device has not regained the expected or desired velocity. The user may, based, for example, on images displayed to her/him (or based on other or additional information that the system may provide her/him with), activate or trigger (by using a user input device) a third force mode (e.g., an emergency force mode) to try move the in-vivo device more vigorously. Location and orientation data collected by the system (e.g., by data recorder 220 of FIG. 2 or data recorder 320 of FIG. 3) may be time stamped and registered/save as the in-vivo device makes its way through the GI system, thus registering the device's entire track. Such data may be beneficial in case there is a need to move the in-vivo device backwards, in the same track. The in-vivo device's track may also be displayed; e.g., on display 303 of FIG. 3.

Figure 11:
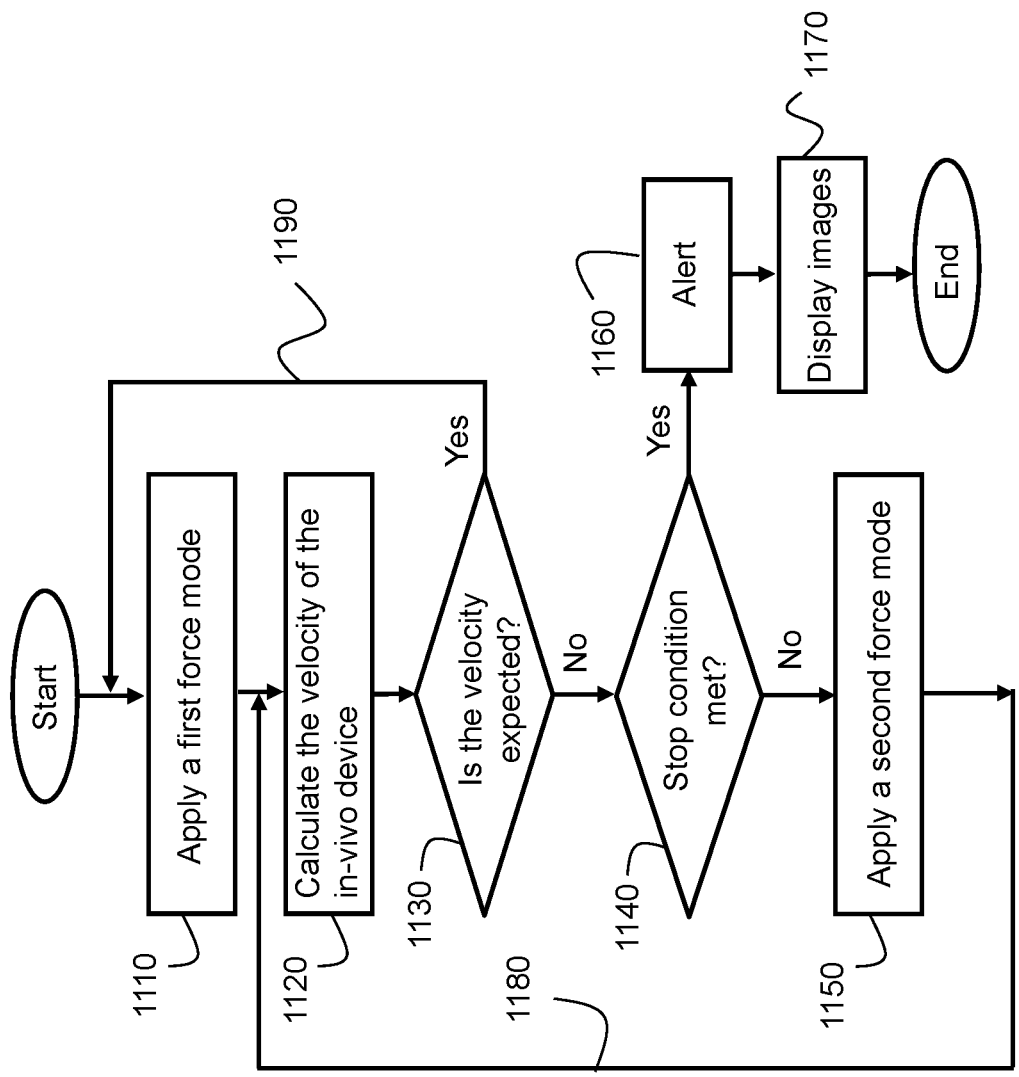
FIG. 11 depicts a velocity-dependent navigation method according to another embodiment of the invention.

FIG. 11 depicts a method for velocity-dependent navigation of an in-vivo device according to an embodiment of the invention. At step 1110, a first force mode may be applied to an in-vivo device while the in-vivo device is in, or moves or advances through, a portion or region of the GI tract, for example through the small intestine. The first force mode may be an initial, or basic, mode of operation during which a magnetic force applied to an in-vivo device may have a 'moderate', or 'basic', magnitude (e.g., approximately 20 gr. force, or so) and also a moderate, or basic, duty cycle that may suffice to subtly, or smoothly, move the in-vivo device in a desired velocity that may depend, for example, on the GI region the in-vivo device is in.

At step 1120, the velocity of the in-vivo device may be calculated, for example, from location information that may be collected while the in-vivo device moves through the GI tract, and, at step 1130, it is checked whether the calculated velocity is the expected velocity or desired velocity. If it is determined that the calculated velocity is the expected or desired velocity (the condition is shown as "Yes" at step 1130), the same (first) force mode may still be used (e.g., step 1110 may be reiterated). However, if it is determined that the calculated velocity is neither the expected velocity nor the desired velocity (the condition is shown as "No" at step 1130), it is checked, at step 1140, whether a "Stop" condition is satisfied. If the "Stop" condition is not satisfied (the condition is shown as "No" at step 1140), a second force mode may operationally replace the first force mode, as per step 1150. Characteristics of the second force mode may be set based on whether the calculated velocity is greater or smaller than the expected or desired velocity. For example, the magnitude of the magnetic force and/or the duty cycle of the magnetic force cycle (MFC) may be manipulated, for example, as described in connection with FIGS. 8 and 9, in order to decrease the velocity if it is too high, or to increase the velocity if it is too low.

After the second force mode is applied for a short while (e.g., half a second), the (actual) velocity of the in-vivo device may be recalculated, at step 1120, rechecked at step 1130, and so on. Loop 1180 may be reiterated every time the calculated velocity deviates from the expected or desired velocity. Loop 1190 may be reiterated every time the calculated velocity is the expected or desired velocity, with an acceptable margin.

If the "Stop" condition checked at step 1140 is met (the satisfied condition is shown as "Yes" at step 1140), this may mean that the in-vivo device may be stationary, or that the second force mode is unsuitable for regaining the expected or desired velocity. Therefore, an alert may be presented to a user, at step 1160, audibly or visually, or both audibly and visually, and, at step 1170, and real-time images may be displayed to the use so that the user can assess the location of the in-vivo device in the GI system, and the reason why the in-vivo device has not regained the expected or desired velocity. The user may, based on, for example, images displayed to her/him (or based on other or additional information that the system; e.g., system 200 or 300 may provide her/him with), activate or trigger (by using a user input device) a third force mode (e.g., an emergency force mode) to try move the in-vivo device more vigorously.

Location and orientation data collected by the system (e.g., by data recorder 220 of FIG. 2 or data recorder 320 of FIG. 3) may be time stamped and registered/saved as the in-vivo device makes its way through the GI system, thus registering the device's entire track. Such data may be beneficial in case there is a need to move the in-vivo device backwards, in the same track. The in-vivo device's track may also be displayed; e.g., on display 303 of FIG. 3.

The methods described, for example, in connection with FIGS. 9 and 10 may be used with an in-vivo device that may include or contain a magnetic thrust end (e.g., magnetic thrust end 110 of FIG. 1A) and a steerable head (e.g., steerable end/head 140 of FIG. 1A) opposite to and spaced apart from the magnetic thrust end, and the magnetic thrust end may comprise a magnetic thrust unit (e.g., magnetic thrust unit 120 of FIG. 1A). A similar method may include (i) determining a three-dimensional orientation of the in-vivo device in the GI tract; and (ii) moving the in-vivo device in the GI tract by applying a magnetic force cycle (MFC) that may include an activation time period (a magnetic force activation period; e.g., activation period T, as per FIG. 8, or activation period T1, T2, T3 and T4, as per FIG. 9), during which a magnetic thrust force (MTF) may be induced in the magnetic thrust unit (MTU) so as to move the in-vivo device in a direction coinciding with the determined orientation of the in-vivo device. A MFC may also include an orientation settling period (e.g., orientation settling periods 812 and 822, as per FIG. 8, or orientation settling periods 912, 922 and 932, as per FIG. 9), during which no magnetic thrust force (MTF) is induced, or only a relatively low MTF (e.g., less than 5% of the maximum MTF that is applied during an activation period) is induced in the MTU.

The steps of determining a three-dimensional orientation of the in-vivo device in the GI tract and moving the in-vivo device in the GI tract by applying a magnetic force cycle (MFC) may reiterate; e.g., to move the in-vivo device further, or farther. The method may further include comparing an actual velocity of the in-vivo device (e.g., the velocity calculated at step 1020 or at step 1120) in the gastrointestinal tract to a reference velocity that may be, for example, an expected velocity or a desired velocity, and changing a parameter of the magnetic (thrust) force according to a (calculated) difference between the actual velocity and the reference velocity. The method may include changing the parameter to reduce the difference between the actual velocity and the reference velocity. The parameter may be selected from the group consisting of a magnitude of the magnetic force, a duty cycle of the magnetic force cycle, orientation of the in-vivo device and location of the in-vivo device. The reference velocity may depend (e.g., selected based) on a location of the in-vivo device in the GI tract, or on the orientation of the in-vivo device, or on both location and orientation of the in-vivo device.

It is preferable that an in-vivo device enters the small intestine in the correct orientation; that is such that its steerable/guided end/head is the leading end (is the in-vivo device's end entering the small intestine first), whereas the magnetic thrusting unit (MTU) is at the trailing end (the in-vivo device's end entering the small intestine last). However, it may occur that the in-vivo device is 'ill-oriented' in the sense that the device's MTU entered, or is about to enter, the small intestine first. This ill-orientation may be fixed, for example, by magnetically flipping over, or otherwise manipulating, the in-vivo device to orient it correctly. For example, the in-vivo device's passive progression (progression using only natural peristalsis) may be tracked for X[cm], e.g., for 20 cm, in order to enable the navigation system to (automatically) assess whether the MTU is at the in-vivo device's trailing end (which is preferable), or at the in-vivo device's leading end. Once the correct orientation of the in-vivo device is regained, the automatic maneuvering/navigation method disclosed herein may commence or continue/resume. After the in-vivo device enters the small intestine, its orientation can be determined by determining the orientation of the magnetic dipole of the magnet included in the MTU, e.g., by using a set of magnetometers that may be positioned on the body of the subject swallowing the in-vivo device. The travelling direction of the in-vivo device may be tracked, say, for a few centimeters (e.g., 20 cm), in order to decide whether the orientation of the in-vivo device is the correct one, or not. Alternatively, while the in-vivo device travels for a few centimeters, images taken during the travel may assist in determining whether or not the orientation of the in-vivo device is the correct one.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as storage unit 340, computer-executable instructions such as timing unit 214 and a controller such as controller 360. Some embodiments may be provided in a computer program product that may include a non-transitory machine-readable medium, having stored thereon instructions, which may be used to program a computer, or other programmable devices, to perform methods as disclosed above.

Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of in-vivo devices (e.g., in-vivo devices with one or more imagers, in-vivo devices with no imagers at all, etc.), and to various types of receivers. Hence the scope of the claims that follow is not limited by the disclosure herein.

The invention claimed is:

1. A method for navigating an in-vivo device in the gastrointestinal tract, the in-vivo device comprising an orientation sensor, a magnetic thrust end and a steerable head opposite to and spaced apart from the magnetic thrust end and steerable by a counterforce that the wall of the gastrointestinal tract exerts on the steerable head, the magnetic thrust end comprising at least one magnet, the method comprising:
   generating an electromagnetic field and concurrently sensing the electromagnetic field by the orientation sensor;
   determining an orientation of the in-vivo device from the sensed electromagnetic field; and
   applying a magnetic force cycle comprising:
      a magnetic force activation period during which a magnetic thrust force is induced in the at least one magnet so as to move the in-vivo device in the gastrointestinal tract in a direction that the steerable head is facing; and
      an orientation settling period during which the electromagnetic field is selected to reduce a stabilizing torque to allow the in-vivo device orientation to settle and to change the direction in which the steerable head is facing due to the steerable head contacting a surface;
   wherein the magnetic force cycle is applied intermittently between successive determinations of the orientation of the in-vivo device.

2. The method as in claim 1, wherein during the orientation settling period no magnetic thrust force is induced in the at least one magnet in order to enable the orientation of the in-vivo device to settle after the force activation period ends.

3. A method for navigating an in-vivo device in the gastrointestinal tract, the in-vivo device comprising an orientation sensor, a magnetic thrust end and a steerable head spaced apart from the magnetic thrust end and steerable by a counterforce applied by the wall of the gastrointestinal tract, the magnetic thrust end comprising at least one magnet, the method comprising:
   generating an electromagnetic field and sensing the electromagnetic field by the orientation sensor;
   determining an orientation of the in-vivo device from the sensed electromagnetic field; and
   applying a magnetic force cycle comprising:
      a first period during which a magnetic thrust force is induced in the at least one magnet so as to move the in-vivo device in the gastrointestinal tract in a direction that the steerable head is facing; and
      a second period during which the electromagnetic field is selected to reduce a stabilizing torque to allow the in-vivo device orientation to settle and to change the direction in which the steerable head is facing only due to the steerable head contacting a surface;
   wherein the magnetic force cycle is applied intermittently between determinations of the orientation of the in-vivo device.

* * * * *